(12) United States Patent
McIntosh

(10) Patent No.: US 8,450,366 B2
(45) Date of Patent: May 28, 2013

(54) ISOBENZOFURAN ANALOGS OF SCLEROPHYTIN A

(75) Inventor: Matthias C. McIntosh, Fayetteville, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 258 days.

(21) Appl. No.: 12/803,611

(22) Filed: Jun. 30, 2010

(65) Prior Publication Data

US 2010/0331370 A1    Dec. 30, 2010

Related U.S. Application Data

(60) Provisional application No. 61/269,875, filed on Jun. 30, 2009.

(51) Int. Cl.
*A61K 31/343* (2006.01)
*C07D 307/88* (2006.01)

(52) U.S. Cl.
USPC .......................................... 514/470; 549/466

(58) Field of Classification Search
USPC .......................................... 514/470; 549/466
See application file for complete search history.

(56) References Cited

PUBLICATIONS

Bateman et al., Bioorg. Med. Chem. Lets. (2009), vol. 19, pp. 6898-6901.*
Adam, W., Arias Encarnacion, L.A., "Benzyl Enol Ethers via Decarboxylation of α-Benzyloxy-β-lactones Derived from the Lithium α-Benzyloxy-α-lithioacetate Synthon," Synthesis (1979), pp. 388-390.
Bernardelli, P. and Paquette, L.A., "Survey of Oxygenated 2,11-Cyclized Cembranoids of Marine Origin," Heterocycles vol. 49 (1998), pp. 531-556.
Bernardelli, P. et al., "Total Asymmetric Synthesis of the Putative Structure of the Cytotoxic Diterpenoid (——)—Sclerophytin A and of the Authentic Natural Sclerophytins A and B," Journal of the American Chemical Society—vol. 123, No. 37 (2001), pp. 9021-9032.
Beumer, R. et al., "Synthesis of novel simplified sarcodictyin/eleutherobin analogs with potent microtubule-stabilizing activity, using ring closing metathesis as the key-step," Tetrahedron 59 (2003), pp. 8803-8820.
Britton, R. et al., "Synthetic Transformations of Eleutherobin Reveal New Features of Its Microtubule-Stabilizing Pharmacophore," Journal of the American Chemical Society—vol. 123, No. 35 (2001), pp. 8632-8633.
Chai, Y., Mou, Z. And McIntosh, M.C., "Studies directed toward the synthesis of the massileunicellins. 2," Tetrahedon Lett. Author Manuscript pp. 1-9; published in final edited form as: Tetrahedron 45 (2010), pp. 3269-3272.
Chai, Y., Vicic, D.A. and McIntosh, M.C "Cycloaldol Approach to the Isobenzofuran Core of Eunicellin Diterpenes," Organic Letters—vol. 5, No. 7 (2003), pp. 1039-1042.

Chandrasekhar, S. et al., "Design, synthesis and cytotoxic studies on the simplified oxy analog of eleutherobin," Bioorganic & Medicinal Chemistry Letters 14 (2004), pp. 3687-3689.
Chiang, G.C.H. et al., "Synthesis of a simplified analogue of eleutherobin via a Claisen rearrangement and ring closing metathesis strategy," Chemical Communications—Issue 14 (2005), pp. 1860-1862.
Ciomei, M. et al., "Sarcodictyins: A new class of marine derivatives with mode of action similar to Taxol," Proceedings of the American Association of Cancer Researchers—vol. 38 (1997), p. 5.
D'Ambrosio, M., Guerriero, A., and Pietra, F., "Isolation from the Mediterranean Stoloniferan Coral Sarcodictyon roseum of Sarcodictyin C, D, E, and F, Novel Diterpenoidic Alcohols Esterified by (E)- or (Z)-N(1)-Methylurocanic Acid. Failure of the Carbon-Skeleton Type as a Classification Criterion," Helvetica Chimica Acta—vol. 71 (1988), pp. 964-976.
D'Ambrosio, M., Guerriero, A., and Pietra, F., "Sarcodictyin A and Sarcodictyin B, Novel Diterpenoidic Alcohols Esterified by (E)-N(1)-Methylurocanic Acid. Isolation from the Mediterranean Stolonifer Sarcodictyon roseum," Helvetica Chimica Acta—vol. 70 (1987), pp. 2019-2027.
Dauben, W.G. And Michno, D.M., "Direct Oxidation of Tertiary Allylic Alcohols. A Simple and Effective Method for Alkylative Carbonyl Transposition," The Journal of Organic Chemistry—vol. 42, No. 4 (1977), pp. 682-685.
Davidson, J.E.P. et al., "The Synthesis and Biological Evaluation of Novel Eunicellin Analogues," Synlett 2004, No. 8, pp. 1434-1436.
Fan, M., Du, L., Stone, A.A., et al., "Modulation of Mitogen-activated Protein Kinases and Phosphorylation of Bcl-2 by Vinblastine Represent Persistent Forms of Normal Fluctuations at G2-M," Cancer Research 60 (2000), pp. 6403-6407.

(Continued)

*Primary Examiner* — Taofiq A Solola
(74) *Attorney, Agent, or Firm* — J. Clinton Wimbish; Smith Moore Leatherwood LLP

(57) ABSTRACT

Isobenzofuran analogs of sclerophytin A are prepared in a highly concise fashion via an aldol-cycloaldol sequence. The analogs exhibit $IC_{50}$'s as low as 1 µM in growth inhibitory studies against KB3 cells using an MTT assay. Preferred analogs have one of the following structural formulas, where R is hydrogen or a substituted or unsubstituted lower alkyl group and Ar is a substituted or unsubstituted aryl group.

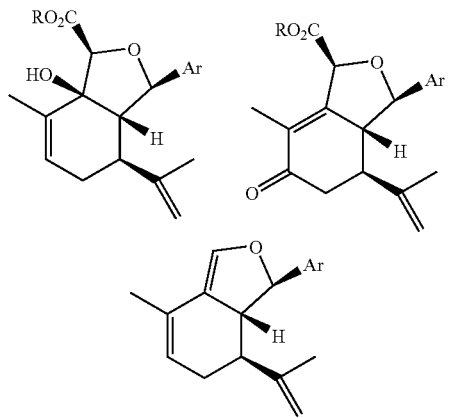

10 Claims, 4 Drawing Sheets

PUBLICATIONS

Friedrich, D., Doskotch, R.W., and Paquette, L.A., "Revised Constitution of Sclerophytins A and B," Organic Letters—vol. 2, No. 13 (2000), pp. 1879-1882.

Hamel, E., Sackett, D.L., Vourloumis, D., and Nicolaou, K.C., "The Coral-Derived Natural Products Eleutherobin and Sarcodictyins A and B: Effects on the Assembly of Purified Tubulin with and without Microtubule-Associated Proteins and Binding at the Polymer Taxoid Site," Biochemistry—vol. 38, No. 17 (1999), pp. 5490-5498.

Jung, M.E. And Pontillo, J., "Synthetic Approach to Analogues of the Original Structure of Sclerophytin A," The Journal of Organic Chemistry—vol. 67, No. 19 (2002), pp. 6848-6851.

Lindel, T. et al., "Eleutherobin, a New Cytotoxin that Mimics Paclitaxel (Taxol) by Stabilizing Microtubules," Journal of the American Chemical Society—vol. 119, No. 37 (1997), pp. 8744-8745.

McDaid, H.M. et al., "Structure-activity profiles of eleutherobin analogs and their cross-resistance in Taxol-resistant cell lines," Cancer Chemother Pharmacol 44 (1999), pp. 131 137.

Mosmann, T., "Rapid Colorimetric Assay for Cellular Growth and Survival: Application to Proliferation and Cytotoxicity Assays," Journal of Immunological Methods, 65 (1983), pp. 55 63.

Nicolaou, K.C. et al., "Total Synthesis of Eleutherobin and Eleuthosides A and B," Journal of the American Chemical Society—vol. 120, No. 34 (1998), pp. 8674-8680.

Nicolaou, K.C. et al., "Total Synthesis of Sarcodictyins A and B," Journal of the American Chemical Society—vol. 120, No. 34 (1998), pp. 8661-8673.

Nicolaou, K.C. et al., "Solid and Solution Phase Synthesis and Biological Evaluation of Combinatorial Sarcodictyin Libraries," Journal of the American Chemical Society—vol. 120, No. 42 (1998), pp. 10814-10826.

Roberge, M., Cinel, B., Anderson, H.J. et al., "Cell-based Screen for Antimitotic Agents and Identification of Analogues of Rhizoxin, Eleutherobin, and Paclitaxel in Natural Extracts," Cancer Research 60 (2000), pp. 5052-5058.

Sharma, P. and Alam, M., "Sclerophytins A and B. Isolation and Structures of Novel Cytotoxic Diterpenes from the Marine Coral Sclerophytum capitalis," Journal of the Chemical Society, Perkin Transactions 1 (1988), pp. 2537-2540.

Steg, Ph. G, et al., "ESC Guidelines for the management of acute myocardial infarction in patients presenting with ST-segment elevation," European Heart Journal (2012) 33, pp. 2569 2619.

Wahlberg, I. and Eklund, A.-M., "Cyclized Cembranoids of Natural Occurrence," Progress in the Chemistry of Organic Natural Products vol. 60 (1992), pp. 1-141.

* cited by examiner

ISOBENZOFURAN ANALOGS OF SCLEROPHYTIN A

REFERENCE TO RELATED APPLICATION

The present application claims the benefit of U.S. Provisional Application No. 61/269,875, filed Jun. 30, 2009, the disclosure of which is incorporated by reference herein.

STATEMENT OF GOVERNMENT SUPPORT

The present invention has been supported in part by NIH Grants CA75577, RR15569, CA125602 and CA109821. The Government has certain rights in the invention.

FIELD OF THE INVENTION

The present invention relates to isobenzofurans, particularly compounds structurally related to sclerophytin A, having anti-cancer and/or antibiotic activities.

BACKGROUND OF THE INVENTION

The 2,11-cyclized cembranoids are a class of diterpenoids isolated from a variety of marine sources that display a range of biological activities.(1) Some 2,11-cyclized cembranoids reported to possess cytotoxic activity are shown below:

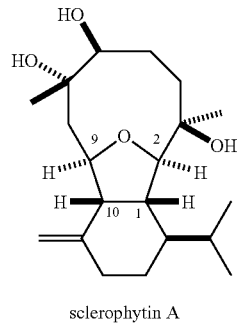

sclerophytin A

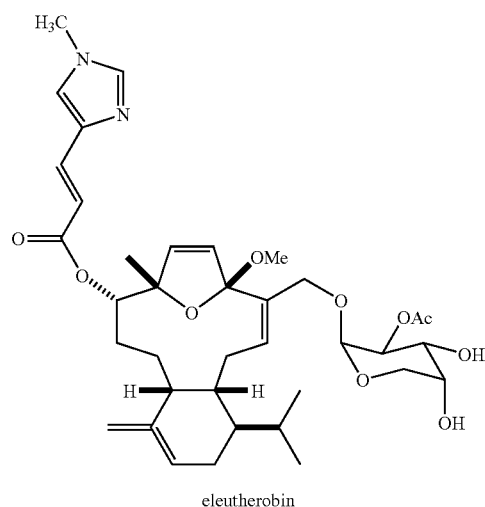

eleutherobin

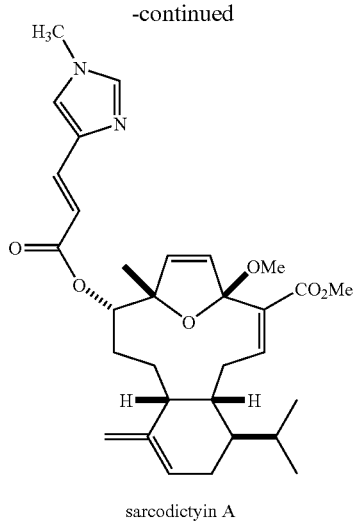

sarcodictyin A

Sclerophytin A has been reported to exhibit growth inhibitory activity against the L1210 cell line with an $IC_{50}$ of 1.0 ng/mL (3 nM).(2-4) Eleutherobin(5,6) and sarcodictyins(7,8) A and B are reported to exhibit taxol-like anti-mitotic activity. (9,10) There have been several reports of structure/activity relationship studies of sarcodictyin (11,12) or eleutherobin (13-16) analogs. However, there are fewer biological studies of any analogs of the more common isobenzofuran-containing 2,11-cyclized cembranoids.(17,18)

Recently, synthetic approaches have been developed for making selected cyclized cembranoids in which the isobenzofuran bicycle is assembled in as few as three steps from commercially available (S)-(+)-carvone using a highly stereoselective aldol-cycloaldol sequence.(19) This approach is used herein to prepare structurally related isobenzofurans that are nominal analogs of sclerophytin A.

SUMMARY OF THE INVENTION

The present invention is directed to novel isobenzofuran analogs of sclerophytin A, which have anti-cancer and/or antibiotic properties. Some preferred compounds of the present invention have one of the following basic structural formulas:

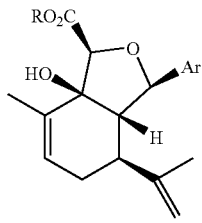

5

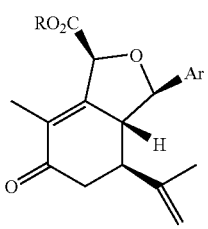

6

-continued

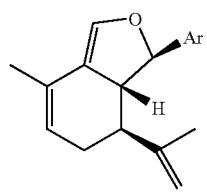

In the formulas, R represents H, or a lower alkyl group, which is substituted or unsubstituted, and Ar represents a substituted or unsubstituted aryl group. A particularly preferred compound has formula 10, wherein Ar is 2-fluorophenyl (herein referred to as compound 10h). A compound of the present invention can have a structure indicated above, or can be provided as a pharmaceutically acceptable ester, salt, or prodrug that releases a compound of the invention when metabolized.

Also contemplated is a method of treating a patient suffering from cancer or a microbial infection comprising administering to the patient a therapeutically effective amount, i.e., one that inhibits proliferation of the cancer or microbial cells, of a compound of the present invention.

DETAILED DESCRIPTION OF THE INVENTION

Figure 1A:
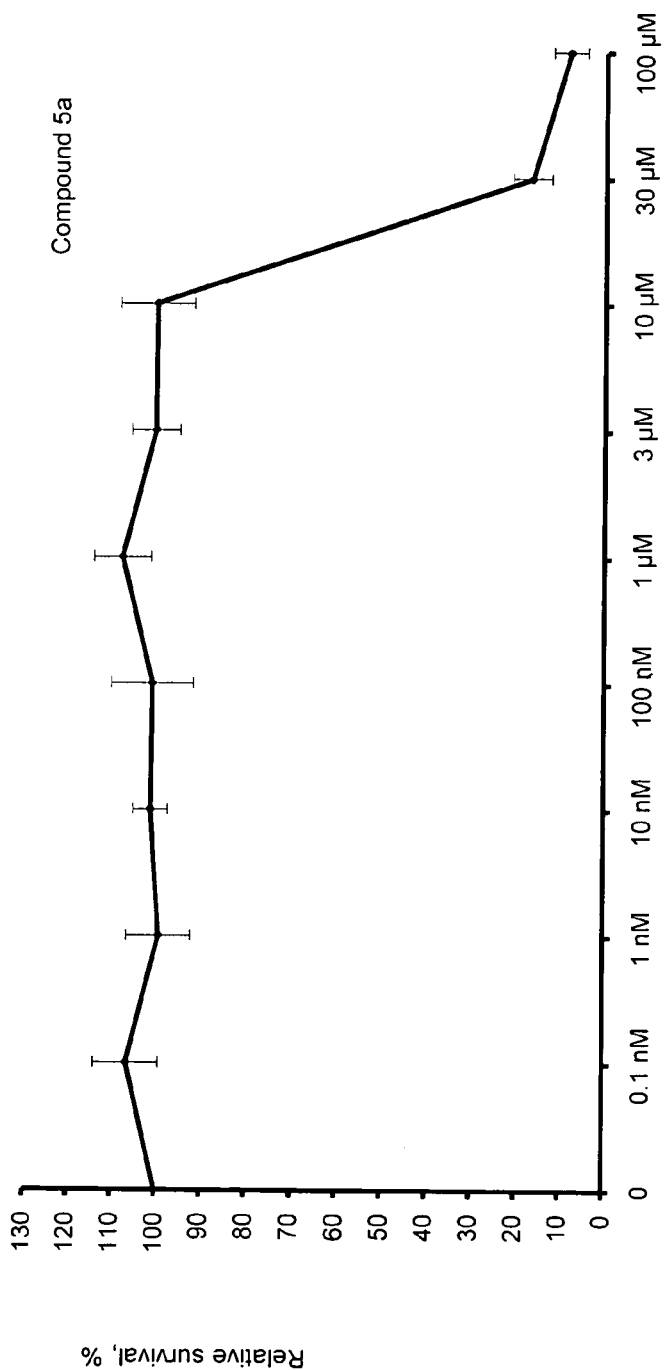
FIGS. 1A-D show the results of inhibition studies of KB-3 cell viability for some selected isobenzofuran compounds (Panel 1A: 5a; Panel 1B: 5c; Panel 1C: 6a; Panel 1D: 8). Cells were treated with increasing concentration of compounds and MTT viability assays were performed after 96 hours. Values are the means of triplicate assays and are expressed as mean±standard deviation relative to control (untreated cells). Note—the X-axis has a non-linear scale.

A compound of the present invention has a chemical structure selected from the following formulas:

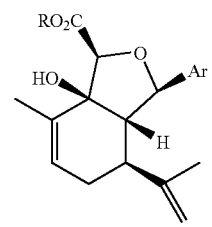

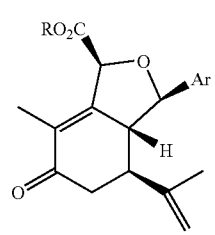

-continued

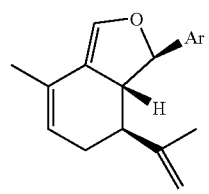

In the formulas, R represents H, a substituted lower alkyl group, or an unsubstituted lower alkyl group. Ar represents a substituted or unsubstituted aryl group. Pharmaceutically acceptable esters, salts, and prodrugs of such compounds are also contemplated within the scope of the invention.

Preferably, in the formulas R=methyl, ethyl, cyclopropylmethyl or cyclopentylmethyl. It is also preferred that Ar=2-Br-phenyl, 3-Br-phenyl, 2,3-di-Cl-phenyl, 2,4-di-Cl-phenyl, 1-naphthyl, 2-pyridyl, 2-furyl, or 2-fluoropheynyl. A particularly preferred compound has structure 10, wherein Ar=2-fluorophenyl.

A method of synthesizing a compound of the present invention comprises converting (S)-(+)-carvone to an aryl glycolate derivative thereof. The conversion comprises reacting (S)-(+)-carvone with an arylaldehyde in an aldol condensation reaction to afford an aryl anti-alcohol, and etherifying the aryl anti-alcohol to afford the aryl glycolate derivative. The aryl glycolate derivative can then be cyclized to afford an isobenzofuran having structural formula 5. The isobenzofuran can then be converted by oxidative rearrangement to an enone having structural formula 6. Alternatively, the aryl glycolate derivative can be converted by β-lactonization-decarboxylation to a diene having structural formula 10.

Synthesis of isobenzofurans of the present invention by cycloaldolization is illustrated in Scheme 1. Intermolecular aldol reaction of (S)-(+)-carvone (1) and aryl aldehydes 2a-f gives anti-aldol adducts 3a-f in moderate to excellent yields and with diastereomer ratios from 1-20:1. Etherification of alcohols 3a-f proceeds in moderate to high yields to give glycolate esters 4a-f. Cycloaldolization under the influence of KHMDS afforded isobenzofurans 5a-f as single diastereomers based on $^1$H NMR analysis.

Sclerophytin A and all other 2,11-cyclized cembranoids possess a C10 stereocenter in the alkane, rather than alcohol, oxidation state. The reduction of alcohols like 5a-d in a 3-step process via the corresponding enone have been previously reported.(19) Hence, enones 6a-d were prepared by oxidative rearrangement of the corresponding 3° alcohols.(20)

Scheme 1: Aldol-cycloaldol synthesis of isobenzofuran compounds 5a-f and 6a-d.

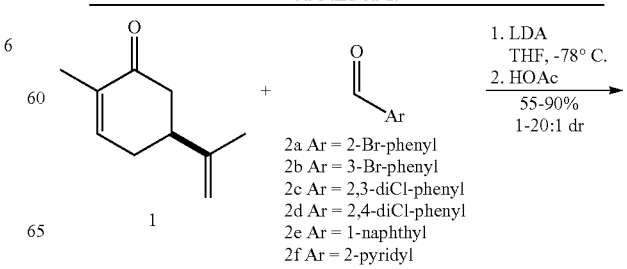

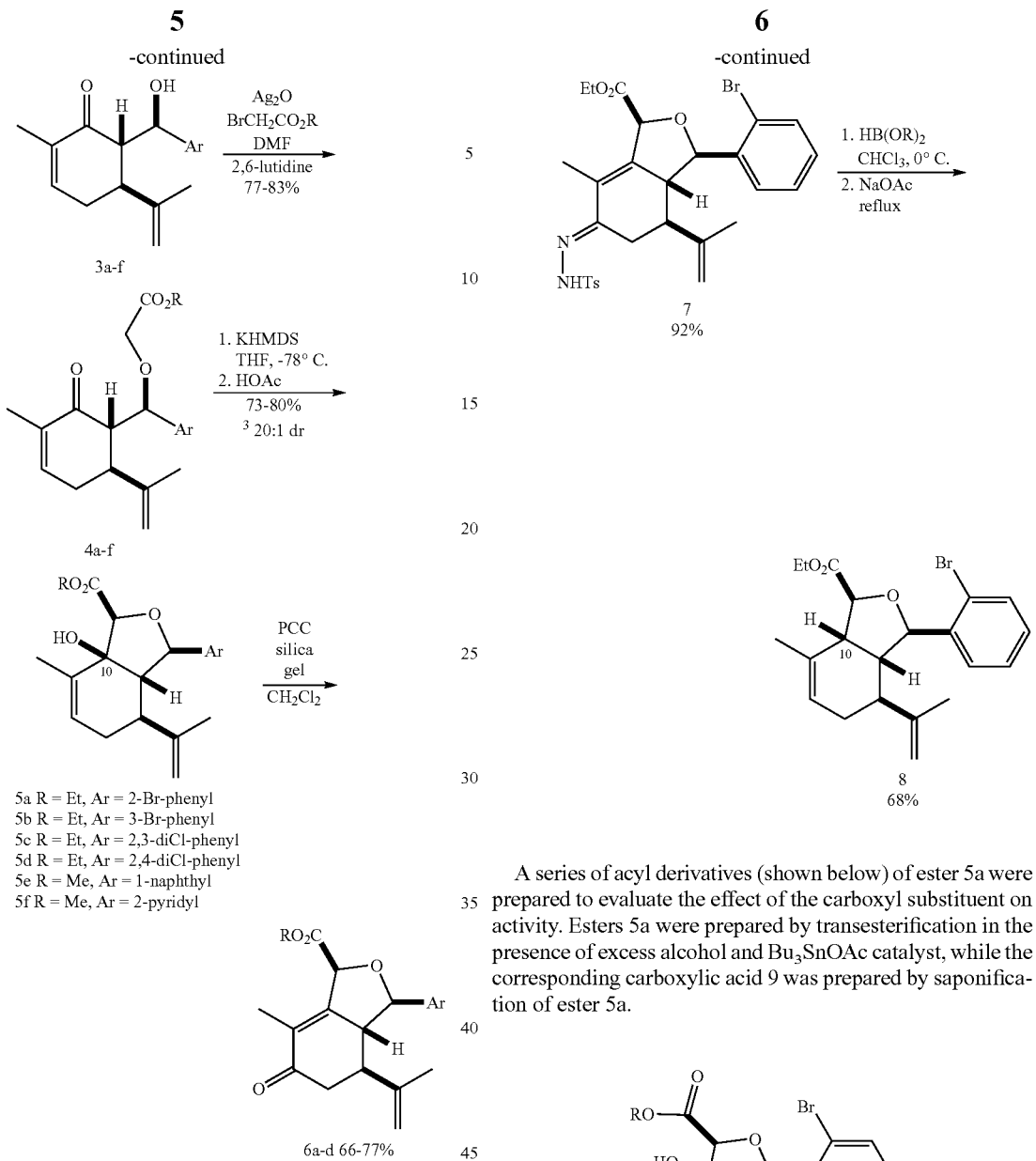

A series of acyl derivatives (shown below) of ester 5a were prepared to evaluate the effect of the carboxyl substituent on activity. Esters 5a were prepared by transesterification in the presence of excess alcohol and $Bu_3SnOAc$ catalyst, while the corresponding carboxylic acid 9 was prepared by saponification of ester 5a.

Reduction of the C10 stereocenter is illustrated by the conversion of enone 6a to tosyl hydrazone 7, which is followed by reductive transposition to afford cis-fused isobenzofuran 8 (Scheme 2).

Scheme 2: Reductive transposition of enone 6a.

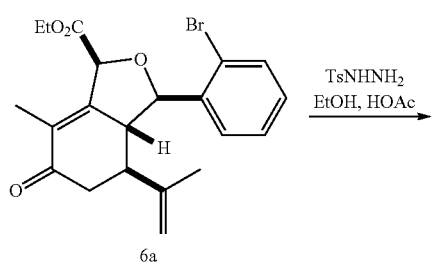

In the course of optimizing the cycloaldol reaction of glycolate 4a to ester 5a, it was found that diene product 10 was formed in significant amounts (ca. 15%) when the reaction mixture is maintained at −78° C. for longer periods of time prior to quenching with HOAc (Scheme 3). For methyl glycolates 4g and 4h, the diene product was the only cyclized product isolated from the reaction mixture. The dienes are presumably formed by lactonization of the aldol intermediates to form unstable β-lactones 11, which upon loss of $CO_2$ afford dienes 10.(21)

Scheme 3: Proposed lactonization-decarboxylation sequence to diene 10.

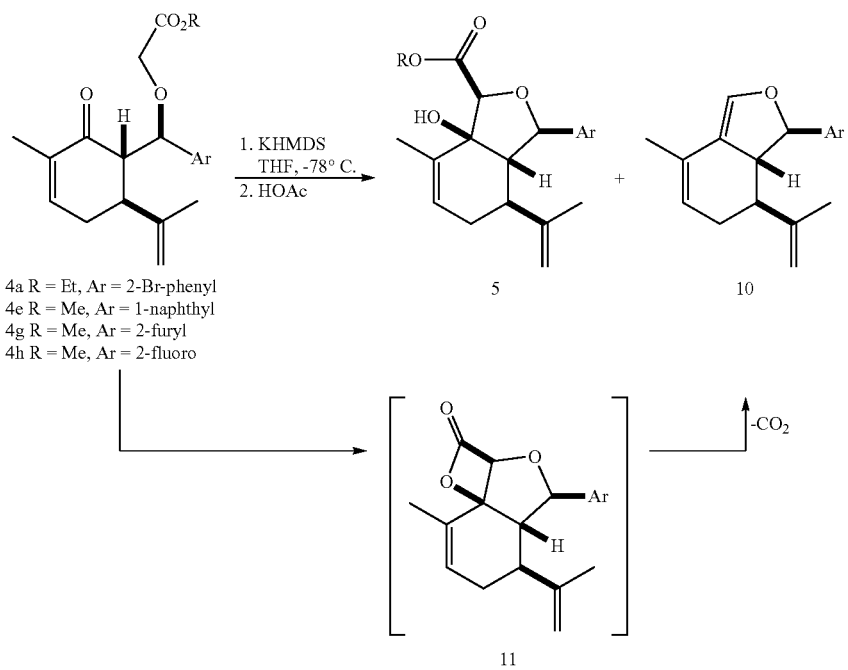

4a R = Et, Ar = 2-Br-phenyl
4e R = Me, Ar = 1-naphthyl
4g R = Me, Ar = 2-furyl
4h R = Me, Ar = 2-fluoro Finally, 2-pyridyl analog 5f was methylated to give pyridinium iodide 5I (Scheme 4). Pyridinium salt 5i could serve as a cationic isostere of 5.a.i.

Scheme 4. Methylation of 2-pyridyl analog 5f.

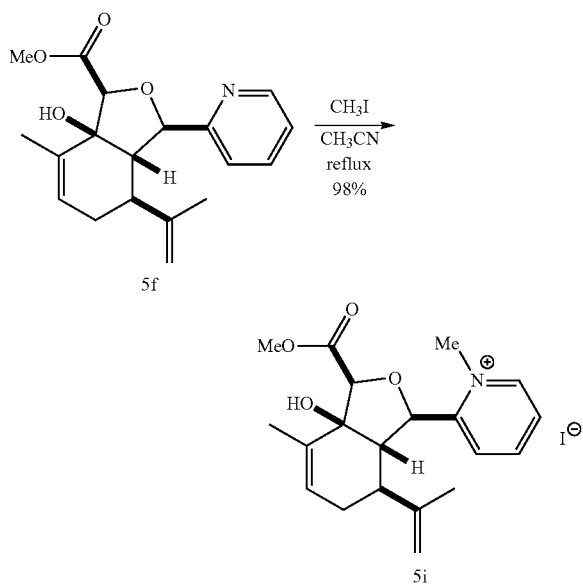

Biological Assays

Figure 1B:
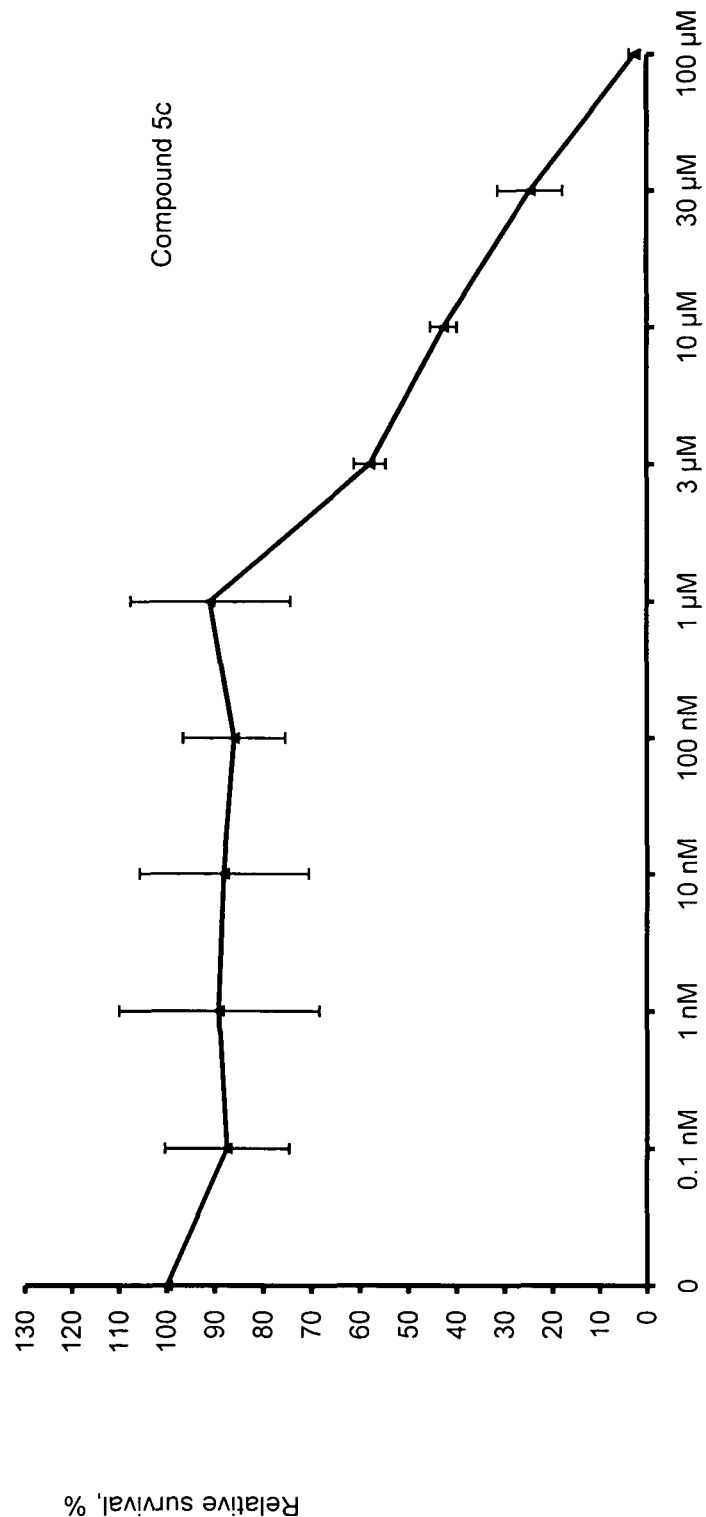
Figure 1C:
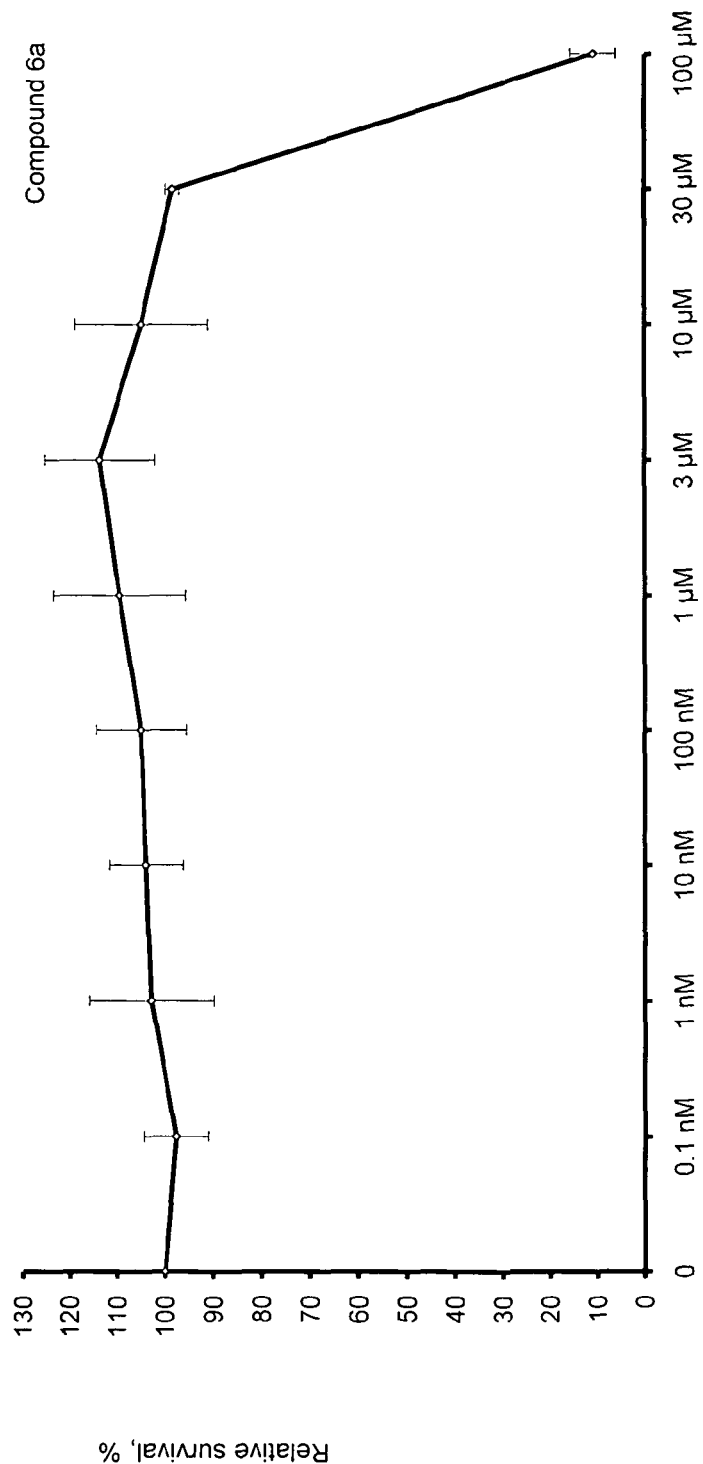
Figure 1D:
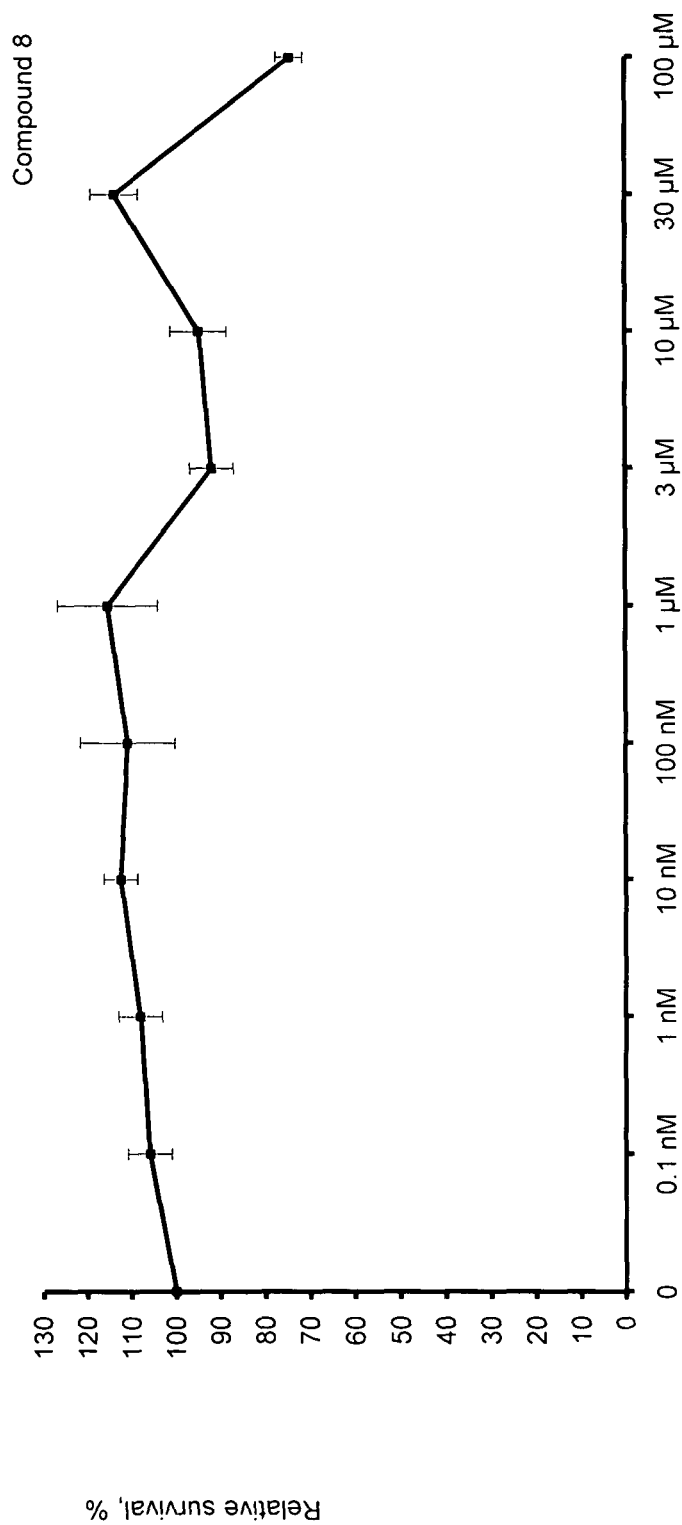

The human KB-3 carcinoma cell line was used to perform the MTT colorimetric assay of cell viability.(22-24) Cells were treated with increasing concentrations of compounds to assess their growth inhibitory properties. $IC_{50}$ values (concentration of the drug required to reduce cell viability by 50%) ranged from 1 to >100 µM (Table 1). The concentration curve for 5c, which had an $IC_{50}$ of 5 µM, is shown in FIG. 1, Panel B. Compounds 5a (FIG. 1, Panel A) and 6a (FIG. 1, Panel C) had higher $IC_{50}$ in the range of 20 and 70 µM, respectively. Several other compounds, e.g., 8 (FIG. 1, Panel D), showed no evident growth inhibitory activity at the highest concentration tested (100 µM).

TABLE 1

Inhibition of KB-3 cell survival assessed by MTT viability assay.

| Entry | Compound | $IC_{50}$ (µM) |
| --- | --- | --- |
| 1 | 5a | 20 |
| 2 | 5a.i | 5 |
| 3 | 5a.ii | 50 |
| 4 | 5a.iii | >100 |
| 5 | 5b | 3 |
| 6 | 5c | 5 |
| 7 | 5d | 3 |
| 8 | 5e | 10 |
| 9 | 5f | 100 |
| 10 | 5i | >100 |
| 11 | 6a | 70 |
| 12 | 6b | 30 |
| 13 | 6c | 5 |
| 14 | 6d | 3 |
| 15 | 8 | >100 |
| 16 | 9 | >100 |
| 17 | 10a | 4 |
| 18 | 10e | >100 |
| 19 | 10g | 2 |
| 20 | 10h | 1 |

Discussion

Several structure-activity trends become apparent upon examination of the assay data. Firstly, for the 2-Br ester compounds 5a (entries 1-6), the smaller the alcohol moiety of the ester, the lower the $IC_{50}$, i.e. Me<Et<cyclopropylmethyl<cyclopentylmethyl~neryl. Secondly, the ethyl ester alcohols 5a-d as a group were more active than the ethyl ester enones 6a-d as a group (entries 1, 5-7 vs. 11-14), with individual differences in the $IC_{50}$ values in the groups varying by factors of 1 to 23.

The essentially equal potency of hydroxy esters 5b-d (entries 5-7) and dienes 10a, g, h (entries 17, 19, 20) is intriguing and suggests that the esters may undergo lactonization and decarboxylation to the dienes in vivo (cf. Scheme 3). This notion is supported by the substantial difference in activity between β-OH ester 5a, which can undergo lactonization, and the corresponding C10 reduction product 8, which cannot (entries 1 and 15, respectively). On the other hand, the 1-napthyl methyl ester 5e (entry 8) is at least 10-fold more active than the corresponding diene 10e (entry 18). Furthermore, enones 6a-d (entries 11-14) exhibit essentially equal potency to the β-OH methyl and ethyl esters, and also cannot undergo β-lactone formation. Further studies would be needed to determine whether β-hydroxy esters 5, enones 6, and dienes 10 are inhibiting growth by the same or different mechanisms of action.

The most active representatives of the compound classes (alcohol 5d, enone 6d and diene 10h) were submitted to NCI's Developmental Therapeutics program for 60-cell line screening. Single dose assays revealed no significant activity for alcohol 5d. Enone 6d exhibited significant differential activity against the RPMI-8226 leukemia and the PC-3 prostate cancer cell lines. Diene 10h was the most active compound tested, possessing significant differential activity against the entire leukemia panel and the NCI-H522 non-small cell lung cancer cell line. Subsequent 5-dose testing of 10h revealed a $GI_{50}=0.148$ µM and $LC_{50}=9.36$ µM for the RPMI-8226 leukemia cell line, and a $GI_{50}=0.552$ µM and $LC_{50}=26.8$ µM for the HOP-92 non-small cell lung cancer cell line.

CONCLUSION

A structurally novel set of analogs has been developed based on the isobenzofuran bicycle common to most of the 2,11-cyclized cembranoids that exhibit $IC_{50}$'s as low as 1 µM for growth inhibition against KB3 cells. Analog 10h possesses sub-micromolar growth inhibitory activity against the RPMI-8226 leukemia and HOP-92 non-small cell lung cancer cell lines.

The present invention is now described with reference to certain examples, which explain but do not limit it.

EXAMPLES

Example 1

Anti-alcohol 3a

To a solution of diisopropylamine (49.9 mmol, 1.5 eq) in dry THF (200 mL) was added n-BuLi (49.9 mmol, 1.5 eq) dropwise at −78° C. under a nitrogen atmosphere. After stirring for 15 min, (S)-(+)-carvone 1 (33.3 mmol, 1 eq) was added drop-wise to the mixture at −78° C. After 30 min 2-bromobenzaldehyde 2a (39.9 mmol, 1.2 eq) was added to the reaction mixture over about 45 min. The mixture was allowed to stir at −78° C. until no starting material was observed by TLC analysis (~6 h). Glacial HOAc (49.9 mmol, 1.5 eq) was then added at −78° C. After stirring ~5 min the reaction was warmed to room temperature (rt) and diluted with 100 mL ether, washed with water (150 mL) and extracted with ether (3×100 mL). The combined organic extracts were then washed with brine, dried over $MgSO_4$, and concentrated in vacuo. The crude product was purified via flash chromatography eluting with 10:90 EtOAc/hexanes to deliver the desired anti-alcohol 3a as a colorless oil (8.56 g, 77%).

$^1$H-NMR (270 MHz, $CDCl_3$) δ 7.63-7.62 (d, 1H), 7.52-7.47 (q, 1H), 7.36-7.34 (m, 1H), 7.14-7.11 (q, 1H), 6.70 (s, 1H), 5.22-5.18 (t, 1H), 4.81-4.73 (d, 2H), 3.20-3.18 (d, 1H), 3.00-2.98 (t, 1H), 2.64-2.68 (m, 2H), 1.77 (s, 3H), 1.67 (s, 3H). $^{13}$C-NMR (270 MHz, $CDCl_3$) δ 200.7, 145.1, 143.7, 141.3, 135.3, 132.7, 129.3, 129.1, 127.6, 113.1, 72.5, 55.1, 44.3, 29.4, 20.9, 15.8. IR (film) 3435, 2922, 2360, 1659 cm$^{-1}$.

Example 2

Anti-alcohol 3b. Following the protocol used for preparation of 3a the desired alcohol 3b was obtained as a colorless oil in 75% (8.17 g, 25.13 mmol) yield from 5g (33.22 mmol) (S)-(+)-carvone. $^1$H-NMR (270 MHz, $CDCl_3$) δ 7.51 (s, 1H), 7.35-7.31 (m, 1H), 7.23-7.20 (t, 1H), 6.71-6.68 (m, 1H), 4.91-4.89 (d, 2H), 4.81-4.76 (dd, 1H), 3.22 (d, 1H), 2.94-2.85 (m, 2H), 2.40-2.43 (m, 2H), 1.74 (s, 3H), 1.53 (s, 3H). $^{13}$C-NMR (270 MHz, $1DCl_3$) δ 201.9, 144.8, 144.1, 142.6, 135.5, 134.5, 133.0, 127.6, 127.1, 113.9, 70.4, 45.6, 31.3, 30.1, 20.6, 15.9

Example 3

Anti-alcohol 3c. Following the protocol used for preparation of 3a the desired alcohol 3c was obtained as a colorless oil in 75% (8.17 g, 25.13 mmol) yield from 5g (33.22 mmol) (S)-(+)-carvone. $^1$H-NMR (270 MHz, $CDCl_3$) δ 7.66-7.63 (d, 1H), 7.38-7.36 (d, 1H), 7.28-7.25 (t, 1H), 6.71-6.69 (m, 1H), 5.24-5.21 (dd, 1H), 4.65-4.60 (d, 2H), 3.16-3.10 (dd, 1H), 3.07-2.95 (m, 2H), 2.46-2.40 (m, 2H), 1.84 (s, 3H), 1.39 (s, 3H). $^{13}$C-NMR (270 MHz, $CDCl_3$) δ 201.9, 144.8, 144.1, 142.6, 135.5, 134.5, 133.0, 127.6, 127.1, 113.9, 70.4, 45.6, 31.3, 30.1, 20.6, 15.9.

Example 4

Anti-alcohol 3d. Following the protocol used for preparation of 3a the desired alcohol 3d was obtained as a colorless oil in 66% yield from 5g (S)-(+)-carvone. $^1$H-NMR (270 MHz, $CDCl_3$) δ 7.65 (d, 1H), 7.31-7.24 (m, 2H), 6.74-6.65 (m, 1H), 5.15-5.08 (dd, J=7.32, 4.75, 1H), 4.88 (s, 1H), 3.26 (d, J=7.32 Hz, 1H), 3.01-2.95 (dd, J=4.75 Hz, 9.3 Hz, 1H), 2.89-2.79 (m, 1H), 2.49 (m, 2H), 1.74 (s, 6H). $^{13}$C-NMR (270 MHz, $CDCl_3$) 201.4, 144.8, 144.1, 139.1, 135.6, 133.6, 132.4, 130.4, 128.9, 127.2, 114.1, 69.7, 54.2, 45.6, 30.2, 20.3, 15.9.

Example 5

Anti-alcohol 3e. Following the protocol used for preparation of 3a the desired alcohol 3e was obtained in 65% yield (2.22 g, 7.25 mmol) from 1.96 g (13.1 mmol) of (S)-(+)-carvone. $^1$H NMR (300 MHz, $CDCl_3$) δ 8.27 (d, J=7.6 Hz, 1H), 8.13 (d, J=7.5 Hz, OH), 7.94-7.78 (m, 3H), 7.62 (d, J=7.2 Hz, 1H), 7.60-7.41 (m, 5H), 6.72 (s, 1H), 5.58 (t, J=6.1 Hz, 1H), 5.16 (s, 1H), 4.82 (d, J=18.7 Hz, 2H), 3.38 (d, J=6.5 Hz, 1H), 3.30-3.20 (m, 1H), 2.72-2.61 (m, 1H), 2.61-2.32 (m, 2H), 1.84 (d, J=1.4 Hz, 3H), 1.61 (s, 3H). $^{13}$C-NMR (75 MHz, $CDCl_3$) δ 201.86, 145.62, 143.77, 137.80, 135.55, 131.34, 128.85, 128.75, 126.52, 126.05, 125.59, 125.50, 123.84, 113.38, 71.11, 63.87, 44.66, 29.39, 21.09, 16.16. Calcd for $C_{21}H_{22}O_2$: C, 82.32; H, 7.24. Found: C, 82.23; H, 7.36.

Example 6

Anti-alcohol 3f. Following the protocol used for preparation of 3a the desired alcohol 3f was obtained in 28% yield (1.92 g, 7.5 mmol) from 4.00 g (26.6 mmol) of (S)-(+)-carvone. $^1$H NMR (300 MHz, CDCl$_3$) δ 8.50 (d, J=4.8 Hz, 1H), 7.68 (td, J=1.7, 7.7 Hz, 1H), 7.51 (d, J=7.6 Hz, 1H), 7.13 (dd, J=4.9, 7.4 Hz, 1H), 6.74-6.65 (m, 1H), 4.94 (dd, J=10.4, 11.8 Hz, 2H), 4.84 (d, J=7.9 Hz, 1H), 3.90 (d, J=9.1 Hz, 1H), 3.50 (dd, J=2.1, 12.4 Hz, 1H), 3.13 (ddd, J=5.1, 10.5, 12.4 Hz, 1H), 2.65-2.47 (m, 1H), 2.39 (dt, J=5.2, 9.5 Hz, 1H), 1.85 (s, 3H), 1.68 (s, 3H). $^{13}$C-NMR (75 MHz, CDCl$_3$) δ 200.91, 163.01, 148.18, 145.60, 144.46, 136.58, 135.88, 121.65, 119.69, 114.48, 72.07, 54.52, 46.27, 31.26, 19.12, 15.84. Calcd for C$_{16}$H$_{19}$NO$_2$: C, 74.68; H, 7.44. Found: C, 74.45; H, 7.50.

Example 7

Anti-alcohol 3g. Following the protocol used for preparation of 3a the desired alcohol 3g was obtained as an oil in 47% yield (1.15 g, 4.7 mmol) from 1.5 g (10.0 mmol) of (S)-(+)-carvone. $^1$H-NMR (300 MHz, CDCl$_3$) δ 7.30 (dd, J=0.8, 1.8 Hz, 1H), 6.78 (ddd, J=1.3, 2.4, 6.1 Hz, 1H), 6.29 (dd, J=1.8, 3.2 Hz, 1H), 6.16 (d, J=3.3 Hz, 1H), 5.20 (d, J=10.9 Hz, 1H), 4.91-4.83 (m, 1H), 4.75 (dd, J=4.5, 11.0 Hz, 2H), 2.95 (dd, J=4.4, 12.8 Hz, 1H), 2.64-2.50 (m, 1H), 2.50-2.34 (m, 1H), 2.33-2.19 (m, 1H), 1.81 (dt, J=1.3, 2.4 Hz, 3H), 1.74 (s, 4H). $^{13}$C-NMR (75 MHz, CDCl$_3$) δ 202.69, 154.94, 154.81, 144.03, 141.68, 135.78, 114.37, 110.23, 108.17, 68.24, 52.10, 45.29, 31.17, 18.74, 15.74. Calcd for C$_{15}$H$_{18}$O$_3$: C, 73.15; H, 7.37. Found: C, 73.39; H, 7.43.

Example 8

Anti-alcohol 3h. Following the protocol used for preparation of 3a the desired alcohol 3h was obtained in 50% yield (1.79 g, 6.52 mmol) from 1.96 g (13.1 mmol) of (S)-(+)-carvone. $^1$H-NMR (300 MHz, CDCl$_3$) δ 7.35 (td, J=1.7, 7.6 Hz, 1H), 7.30-7.14 (m, 1H), 7.07 (dt, J=3.8, 7.5 Hz, 1H), 6.96 (ddd, J=1.2, 8.2, 10.6 Hz, 1H), 6.72 (ddd, J=1.4, 3.6, 4.9 Hz, 1H), 5.39 (dd, J=5.1, 8.1 Hz, 1H), 4.71 (dd, J=12.7, 14.1 Hz, 2H), 4.12 (d, J=8.2 Hz, 1H), 3.03 (dd, J=5.1, 9.8 Hz, 1H), 2.84-2.68 (m, 1H), 2.51-2.25 (m, 2H), 1.77 (s, 3H), 1.58 (s, 3H). $^{13}$C-NMR (75 MHz, CDCl$_3$) δ 202.01, 161.92, 158.66, 145.11, 135.90, 129.28, 129.16, 129.11, 128.99, 124.07, 115.49, 115.19, 113.26, 67.87, 53.89, 43.54, 30.52, 19.83, 16.04. Calcd for C$_{17}$H$_{19}$FO$_2$: C, 74.43; H, 6.98. Found: C, 74.70; H, 7.03.

Example 9

Glycolate 4a. To a stirring solution of alcohol 3a (8.65 g, 25.80 mmol) in anhydrous dimethylformamide (DMF) (75 mL) was added 8.97 g (38.7 mmol, 1.5 eq) Ag$_2$O, followed by dropwise addition of ethyl bromoacetate (4.29 mL, 38.7 mmol) at rt. After stirring ~10 min, 2,6-lutidine (3.1 mL, 38.7 mmol) was added very slowly (~0.2 mL/h) via syringe pump and the mixture was then allowed to stir at rt an additional 24 h. The crude solution was then filtered through a short silica gel column and eluted with diethyl ether. The filtrate was washed with 3N HCl (100 mL) and extracted with hexane (3×60 mL). The combined extracts were washed with saturated aqueous NaHCO$_3$ and brine, then dried over MgSO$_4$, and concentrated in vacuo. The crude mixture was purified via flash chromatography eluting with 20:80 EtOAc/hexanes to yield glycolate 4a as a yellow oil (8.47 g, 78%). $^1$H-NMR (270 MHz, CDCl$_3$) δ 7.54-7.51 (t, 1H), 7.37-7.35 (m, 1H), 7.18-7.16 (t, 1H), 6.61 (s, 1H), 5.23-5.21 (d, 1H), 4.74-4.66 (d, 2H) 4.15-4.12 (m, 1H), 3.99-3.92 (m, 1H), 3.68-3.62 (d, 1H), 3.00-2.97 (m, 2H), 2.53-2.52 (s, 1H), 2.38-2.31 (d, 1H), 1.82, (s, 3H), 1.63 (s, 3H), 1.24-1.19 (t, 3H). $^{13}$C-NMR (270 MHz, CDCl$_3$) 198.3, 169.9, 141.7, 129.8, 129.0, 128.8, 128.1, 127.6, 112.2, 80.7, 77.6, 77.1, 76.6, 65.6, 64.9, 60.7, 55.4, 43.5, 28.4, 21.4, 16.3, 14.2.

Example 10

Glycolate 4b. Following the above procedure for preparation of 4a, glycolate 4b was obtained in 77% yield as a colorless oil from 1.61 g (4.80 mmol) alcohol 3b. $^1$H-NMR (270 MHz, CDCl$_3$) δ 7.53-7.49 (d, 1H), 7.45-7.42 (d, 1H), 7.33-7.27 (t, 1H), 7.18-7.07 (m, 1H), 6.64 (s, 1H), 5.42-5.39 (d, 1H), 4.69-4.64 (d, 2H) 4.23-4.14 (m, 2H), 4.00-3.94 (d, J=16.43, 1H), 3.82-3.76 (d, J=16.43 Hz, 1H), 3.33-3.26 (m, 1H), 2.97-2.92 (m, 2H), 2.43-2.36 (m, 1H), 1.72, (s, 3H), 1.50 (s, 3H), 1.27-1.22 (t, 3H). $^{13}$C-NMR (270 MHz, CDCl$_3$) 197.8, 170.1, 146.1, 143.4, 138.0, 135.5, 132.6, 129.6, 129.4, 127.6, 112.3, 79.4, 72.6, 68.0, 66.2, 61.0, 55.7, 41.5, 28.2, 21.2, 16.3, 14.3.

Example 11

Glycolate 4c. Following the above procedure, glycolate 4c was obtained in 83% yield as a colorless oil from 7.06 g (21.71 mmol) alcohol 3c. $^1$H-NMR (270 MHz, CDCl$_3$) δ 7.53-7.49 (d, 1H), 7.44-7.40 (d, 1H), 7.30-7.26 (m, 1H), 6.64 (s, 1H), 5.20-5.18 (d, 1H), 4.81-4.76 (d, 2H) 4.20-4.11 (m, 2H), 4.03-3.97 (d, J=16.03 Hz, 1H), 3.72-3.66 (d, J=16.03 Hz, 1H), 3.31-3.25 (m, 1H), 2.94-2.90 (m, 2H), 2.44-2.34 (m, 1H), 1.72, (s, 3H), 1.48 (s, 3H), 1.31-1.26 (t, 3H). $^{13}$C-NMR (300 MHz, CDCl$_3$) 198.9, 170.0, 143.5, 129.8, 129.5, 127.4, 127.0, 112.5, 70.7, 68.1, 61.0, 55.1, 41.6, 28.5, 16.2, 14.2.

Example 12

Glycolate 4d. Following the above procedure, glycolate 4d was obtained in 80% yield as a colorless oil from 9.48 g (29.15 mmol) alcohol 3d. $^1$H-NMR (270 MHz, CDCl$_3$) δ 7.53-7.49 (d, 1H), 7.44-7.40 (d, 1H), 7.30-7.26 (m, 1H), 6.64 (s, 1H), 5.20-5.18 (d, 1H), 4.81-4.76 (d, 2H) 4.20-4.11 (m, 2H), 4.03-3.97 (d, J=16.03 Hz, 1H), 3.72-3.66 (d, J=16.03 Hz, 1H), 3.31-3.25 (m, 1H), 2.94-2.90 (m, 2H), 2.44-2.34 (m, 1H), 1.72, (s, 3H), 1.48 (s, 3H), 1.31-1.26 (t, 3H). $^{13}$C-NMR (300 MHz, CDCl$_3$) 198.9, 170.0, 143.5, 129.8, 129.5, 127.4, 127.0, 112.5, 70.7, 68.1, 61.0, 55.1, 41.6, 28.5, 16.2, 14.2.

Example 13

Glycolate 4e. Following the above procedure, glycolate 4e was obtained as an oil in 25% yield (8.17 g, 25.13 mmol) from alcohol 3e (3.27 mmol). $^1$H-NMR (300 MHz, CDCl$_3$) δ 8.09 (d, J=7.6 Hz, 1H), 7.91-7.83 (m, 1H), 7.79 (d, J=8.2 Hz, 1H), 7.60 (d, J=7.0 Hz, 1H), 7.56-7.41 (m, 3H), 6.75 (s, 1H), 5.86 (d, J=5.1 Hz, 1H), 4.59 (s, 2H), 4.13 (d, J=16.4 Hz, 1H), 3.92 (d, J=10.3 Hz, 1H), 3.70 (s, 3H), 3.28 (dd, J=4.4, 9.8 Hz, 1H), 3.09-2.90 (m, 2H), 2.47-2.31 (m, 1H), 1.72 (s, 3H), 1.27 (s, 3H). $^{13}$C-NMR (75 MHz, CDCl$_3$) δ 198.92, 170.89, 146.63, 144.20, 135.41, 134.25, 133.96, 131.11, 129.22, 128.72, 126.54, 125.73, 125.26, 125.22, 122.98, 112.11, 79.47, 66.40, 55.66, 51.85, 41.25, 29.00, 20.97, 16.37. HRMS Calcd for C$_{24}$H$_{26}$O$_4$Na: 401.1729. Found: 401.1719.

Example 14

Glycolate 4f. Following the above procedure, glycolate 4f was obtained as an oil in 86% yield (1.43 g, 4.34 mmol) from 1.3 g (5.05 mmol) of alcohol 3f. $^1$H-NMR (300 MHz, CDCl$_3$)

δ 8.50 (d, J=4.8, 1H), 7.70 (dt, J=7.0, 20.6 Hz, 2H), 7.23-7.10 (m, 1H), 6.63 (s, 1H), 4.83 (s, 1H), 4.75 (d, J=5.2 Hz, 1H), 4.20 (d, J=16.2 Hz, 1H), 3.93 (d, J=16.2 Hz, 1H), 3.69 (s, 3H), 3.17 (dd, J=5.2, 8.0 Hz, 1H), 2.89-2.70 (m, 1H), 2.50 (m, 2H), 1.80-1.71 (m, 6H).
$^{13}$C-NMR (75 MHz, CDCl$_3$) δ 197.99, 170.30, 160.59, 148.74 145.81, 142.32, 136.52, 135.60, 122.39, 121.32, 113.28, 83.42, 67.59, 55.15, 51.80, 44.20, 29.28, 20.03, 16.15. Calcd for $C_{19}H_{23}NO_4$: C, 69.28; H, 7.04. Found: C, 68.99; H, 7.09.

Example 15

Glycolate 4g. Following the above procedure, glycolate 4g was obtained as an oil in 48% yield (679 mg, 2.13 mmol) from 1.1 g (4.46 mmol) of alcohol 3g. $^1$H-NMR (300 MHz, CDCl$_3$) δ 7.40 (dd, J=0.7 Hz, 1.7, 1H), 6.68-6.59 (m, 1H), 6.33-6.20 (m, 2H), 4.88 (d, J=7.6 Hz, 1H), 4.74 (d, J=1.2 Hz, 1H), 4.66 (s, 1H), 4.12 (d, J=16.8 Hz, 1H), 3.96-3.87 (m, 1H), 3.73-3.66 (m, 3H), 3.21 (dd, J=4.4, 9.4 Hz, 1H), 3.09 (dd, J=4.4, 7.5 Hz, 1H), 2.98-2.81 (m, 1H), 2.42 (ddd, J=2.5, 5.6, 19.6 Hz, 1H), 1.68 (s, 7H). $^{13}$C-NMR (75 MHz, CDCl$_3$) δ 198.03, 171.00, 151.32, 145.97, 143.28, 143.06, 112.17, 110.34, 110.18, 74.74, 65.50, 54.79, 51.92, 41.73, 28.02, 21.52, 16.28. Calcd. for $C_{18}H_{22}O_5$: C, 67.91; H, 6.97. Found: C, 67.71; H, 6.96.

Example 16

Glycolate 4h. Following the above procedure, glycolate 4h was obtained as an oil in 19% yield (0.25 g, 0.71 mmol) from 1.05 g of alcohol 3h (3.8 mmol). $^1$H NMR (300 MHz, CDCl$_3$) δ 7.44 (td, J=1.8, 7.5 Hz, 1H), 7.31-7.21 (m, 2H), 7.15 (t, J=7.0 Hz, 1H), 6.97 (dd, J=8.4, 10.1 Hz, 1H), 6.66 (s, 1H), 5.26 (d, J=7.6 Hz, 1H), 4.68 (d, J=11.6 Hz, 2H), 4.08 (d, J=16.5 Hz, 1H), 3.87 (d, J=16.5 Hz, 1H), 3.73 (s, 3H), 3.31 (s, 1H), 3.06-2.80 (m, 2H), 2.43 (d, J=19.6 Hz, 1H), 1.72 (s, 3H), 1.59 (s, 3H). $^{13}$C-NMR (75 MHz, CDCl$_3$) δ 198.18, 170.72, 162.47, 159.21, 146.07, 143.16, 135.39, 129.84, 128.75, 126.14, 125.97, 124.48, 124.43, 115.46, 115.18, 112.2574.74, 66.05, 56.64, 51.90, 41.50, 27.91, 21.48, 16.24. Calcd for $C_{20}H_{23}FO_4$: C, 69.35; H, 6.69. Found: C, 68.98, H, 6.61.

Example 17

Isobenzofuran 5a. To a 0.1 M solution of glycolate 4a (4.13 g, 9.8 mmol) in dry
THF (100 mL) was added potassium bis(trimethylsilylamide) (KHMDS) (23.53 mL, 11.76 mmol, 1.1 eq, 0.5 M soln. in toluene) quickly at –78° C., followed immediately by rapid addition of 1.2 eq HOAc (0.673 mL, 11.76 mmol). The reaction mixture was allowed to warm to rt before water (100 mL) was added and the organic layer was extracted with ether (3×60 mL). The combined extracts were washed with brine and dried over MgSO$_4$, filtered and concentrated in vacuo. The crude product was purified via flash chromatography with 10:90 EtOAc/hexanes to yield the desired cycloaldol product 5a as a colorless oil (3.30 g, 7.84 mmol, 80%). $^1$H-NMR (270 MHz, CDCl$_3$) δ 8.26-8.22 (d, 1H), 7.50-7.48 (d, 1H), 7.40-7.38 (t, 1H), 7.15-7.13 (t, 1H), 5.73 (s, 1H), 5.22-5.18 (d, 1H), 4.80 (s, 2H), 4.42 (s, 1H), 4.28-4.25 (m, 2H), 2.74-2.69 (m, 1H), 2.58-2.42 (d, 1H), 2.28-2.27 (m, 2H), 1.82 (s, 3H), 1.53 (s, 3H), 1.33-1.28 (t, 3H). $^{13}$C-NMR (270 MHz, CDCl$_3$) 171.0, 147.0, 139.4, 132.9, 132.4, 130.4, 129.7, 128.3, 125.6, 123.9, 112.2, 82.6, 81.9, 80.7, 61.3, 55.5, 39.1, 27.7, 21.4, 17.7, 14.2.

Example 18

Isobenzofuran 5b. Following the same procedure used for preparing 5a, isobenzofuran 5b was obtained in 73% yield as a pale yellow oil from 0.77 g (1.83 mmol) glycolate 4b. $^1$H-NMR (270 MHz, CDCl$_3$) δ 8.31-8.26 (d, 1H), 7.54-7.49 (d, 1H), 7.46-7.39 (t, 1H), 7.20-7.13 (t, 1H), 5.79-5.74 (m, 1H), 5.27-5.21 (d, 1H), 4.83 (s, 2H), 4.45 (s, 1H), 4.35-4.23 (m, 2H), 3.09 (s, 1H), 2.79-2.71 (dd, 1H), 2.60-2.47 (m, 1H), 2.35-2.22 (m, 2H), 1.86 (s, 3H), 1.57 (s, 3H), 1.39-1.30 (t, 3H). $^{13}$C-NMR (270 MHz, CDCl$_3$) 171.0, 146.9, 139.4, 132.9, 132.4, 130.4, 129.7, 128.3, 125.6, 123.8, 112.1, 82.6, 81.8, 80.6, 61.3, 55.5, 39.0, 27.7, 21.4, 17.7, 14.15.

Example 19

Isobenzofuran 5c. Following the same procedure used for preparing 5a, isobenzofuran 5c was obtained in 77% yield as a pale yellow oil from 3.39 g (8.24 mmol) glycolate 4c. $^1$H-NMR (270 MHz, CDCl$_3$) δ 8.26-8.16 (d, 1H), 7.42-7.34 (d, 1H), 7.32-7.21 (t, 1H), 5.71 (s, 1H), 5.34-5.26 (d, 1H), 4.79 (s, 2H), 4.42 (s, 1H), 4.34-4.14 (m, 2H), 3.06 (s, 1H), 2.72-2.61 (dd, 1H), 2.49-2.16 (m, 3H), 1.81 (s, 3H), 1.54 (s, 3H), 1.35-1.20 (t, 3H). $^{13}$C-NMR (270 MHz, CDCl$_3$) 171.1, 146.7, 140.8, 132.9, 132.6, 131.5, 130.1, 128.4, 128.1, 125.7, 112.5, 81.9, 80.9, 80.7, 61.4, 55.4, 39.7, 27.7, 21.3, 17.7, 14.2.

Example 20

Isobenzofuran 5d. Following the same procedure used for preparing 5a, isobenzofuran 5d was obtained in 74% yield as a pale yellow oil from 4.73 g (11.50 mmol) glycolate 4d. $^1$H-NMR (270 MHz, CDCl$_3$) δ 8.30-8.25 (d, 1H), 7.39-7.32 (m, 2H), 5.75 (S, 1H), 5.29-5.23 (d, 2H), 4.84 (s, 2H), 4.46 (s, 1H), 4.37-4.22 (m, 2H), 3.16 (s, 1H), 2.73-2.64 (m, 1H), 2.50-2.19 (m 3H), 1.85 (s, 3H), 1.59 (s, 3H), 1.38-1.31 (t, 2H).

Example 21

Isobenzofuran 5e. Following the same procedure used for preparing 5a, isobenzofuran 5e was obtained in 59% yield (0.22 g, 0.59 mmol) from 0.41 g (1.08 mmol) of glycolate 4e. $^1$H-NMR (300 MHz, CDCl$_3$) δ 8.34 (d, J=8.0 Hz, 1H), 8.16 (d, J=7.2 Hz, 1H), 7.86 (t, J=9.1 Hz, 2H), 7.52 (dt, J=6.9, 14.5 Hz, 3H), 5.76 (s, 1H), 5.62 (d, J=7.2 Hz, 1H), 4.91 (s, 1H), 4.83 (s, 1H), 4.59 (s, 1H), 3.85 (s, 3H), 3.26 (s, 1H), 3.03 (t, J=7.2 Hz, 1H), 2.39 (dd, J=6.5, 12.7 Hz, 1H), 2.29 (s, 2H), 1.87 (s, 3H), 1.55 (s, 3H). $^{13}$C-NMR (75 MHz, CDCl$_3$) δ 172.29, 146.85, 135.72, 133.92, 133.46, 131.85, 128.99, 128.86, 126.11, 125.74, 125.63, 125.60, 125.52, 123.60, 113.03, 82.77, 81.51, 80.99, 53.68, 52.36, 42.04, 28.22, 20.68, 17.79. Calcd for $C_{24}H_{26}O_4$: C, 76.17; H, 6.92. Found: C, 76.09; H, 6.95.

Example 22

Isobenzofuran 5f. Following the same procedure used for preparing 5a, isobenzofuran 5f was obtained in 81% yield (0.30 g, 0.90 mmol) from 0.36 g (1.10 mmol) of glycolate 4f. $^1$H-NMR (300 MHz, CDCl$_3$) δ 8.53 (d, J=4.0 Hz, 1H), 7.64 (td, J=1.8, 7.7 Hz, 1H), 7.19 (ddd, J=3.6, 6.0, 7.8 Hz, 2H), 5.58 (d, J=1.5 Hz, 1H), 4.88 (s, 1H), 4.82 (s, 1H), 4.55 (s, 1H), 3.69 (s, 3H), 2.55-2.32 (m, 2H), 2.07 (d, J=3.1, 2H), 1.89-1.73 (m, 3H), 1.50 (s, 3H). $^{13}$C-NMR (75 MHz, CDCl$_3$) δ 170.36, 159.63, 149.19, 146.18, 137.80, 133.65, 125.22, 123.42, 123.23, 113.50, 87.12, 84.83, 82.53, 54.58, 52.07, 46.56, 30.98, 19.36, 17.95. HRMS Calcd for $C_{19}H_{23}NO_4$: C, 69.28; H, 7.04. Found: C, 68.98; H, 6.86.

Example 23

Enone Ester 6a. To a solution of isobenzofuran 5a (0.37 g, 0.87 mmol) in anhydrous $CH_2Cl_2$ (9.0 mL) was added premixed mixture of pyridinium chlorochromate (PCC) (2.0 g, 8.7 mmol)/silica gel (2.0 g) and 3-4 drops of anhydrous toluene. The reaction mixture was allowed to stir at rt for 24 h, then was filtered through a short silica gel column with ether (100 mL). The eluant was concentrated in vacuo and the dark brown residue was purified via flash chromatography over silica gel (85/15, hexane/EtOAc) to afford enone 6a as a white solid (0.2 g, 55%). $^1$H-NMR (270 MHz, $CDCl_3$) δ 8.12-7.90 (d, 1H), 7.50-7.30 (m, 2H), 7.12-7.08 (d, 1H), 5.30 (s, 1H), 5.20-5.10 (d, 1H), 4.70 (s, 1H), 4.40 (s, 1H), 4.28-4.18 (m, 2H), 3.30-3.10 (m, 1H), 2.85-2.70 (m, 1H), 2.45-2.31 (m, 2H), 1.90 (s, 3H), 1.40 (t, 3H), 1.20 (s, 3H). $^{13}$C-NMR (270 MHz, $CDCl_3$) 198.0, 171.0, 146.0, 142.0, 138.0, 132.9, 130.4, 130.0, 129.7, 128.3, 125.6, 114.2, 85.2, 78.5, 62.3, 51.5, 47.5, 42.0, 18.5, 14.7, 12.2.

Example 24

Enone ester 6b. Following the same procedure used for preparing 6a, enone 6b was obtained in 54% yield as a white solid from 0.124 g (0.294 mmol) isobenzofuran 5b. $^1$H-NMR (270 MHz, $CDCl_3$) δ 8.04-7.99 (d, 1H), 7.51-7.47 (d, 1H), 7.45-7.38 (t, 1H), 7.21-7.15 (t, 1H), 5.30-5.27 (m, 1H), 5.24-5.19, (d, 1H), 4.74 (s, 1H), 4.47 (s, 1H), 4.36-4.27 (q, J=7.11 Hz, 2H), 3.31-3.21 (m, 1H), 2.88-2.77 (m, 1H), 2.49-2.34 (m, 2H), 1.93 (s, 1H), 1.41-1.34 (t, J=7.11 Hz, 3H), 1.27 (s, 3H). $^{13}$C-NMR (270 MHz, $CDCl_3$) 183.6, 156.0, 142.3, 132.6, 129.9, 127.9, 113.9, 85.0, 78.1, 66.6, 62.0, 58.0, 46.7, 42.4, 22.7, 18.02, 14.2, 11.4.

Example 25

Enone ester 6c. Following the same procedure used for preparing 6a, enone 6c was obtained in 56% yield as a white solid from 0.0.4 g (0.972 mmol) isobenzofuran 5c. $^1$H-NMR (270 MHz, $CDCl_3$) δ 7.94-7.91 (d, 1H), 7.36-7.35 (d, 1H), 7.28-7.24 (t, 1H), 5.28-5.23 (d, 2H), 4.61 (s, 1H), 4.41 (s, 1H), 4.26-4.18 (m, 2H), 3.21-3.08 (m, 1H), 2.80-2.65 (m, 1H), 2.35-2.23 (m, 2H), 1.85 (s, 3H), 1.25 (t, 3H), 1.20 (s, 3H). $^{13}$C-NMR (270 MHz, $CDCl_3$) 197.5, 169.8, 154.7, 142.1, 139.0, 132.5, 129.9, 127.4, 113.4, 82.6, 62.0, 50.4, 46.9, 42.3, 18.2, 14.1, 11.1.

Example 26

Enone ester 6d. Following the same procedure used for preparing 6a, enone 6d was obtained in 67% yield as a white solid from 0.17 g (0.41 mmol) isobenzofuran 5d. $^1$H-NMR (270 MHz, $CDCl_3$) δ 7.97-7.94 (d, 1H), 7.36-7.23 (m, 2H), 5.23 (s, 1H), 5.15-5.11 (d, 1H), 4.66 (s, 1H), 4.46 (s, 1H), 4.31-4.21 (m, 2H), 3.21-3.11 (m, 1H), 2.80-2.69 (m, 1H), 2.46-2.29 (m, 2H), 1.88 (s, 3H), 1.35-29 (t, 3H), 1.26 (s, 3H). $^{13}$C-NMR (270 MHz, $CDCl_3$) 198.1, 169.8, 155.5, 142.4, 135.6, 134.7, 130.5, 130.4, 129.0, 127.8, 114.0, 82.0, 62.2, 50.2, 46.7, 42.3, 18.2, 14.3, 11.5.

Example 27

Tosylhydrazone 7. HOAc (0.01 g, 0.16 mmol) was added to a solution of enone ester 6a (0.10 g, 0.24 mmol) and tosylhydrazide (0.06 g, 0.31 mmol) in $CH_2Cl_2$ (2.20 mL). The reaction mixture stirred at rt for 24 h, then was washed with water (5.00 mL), dried over $MgSO_4$, filtered and concentrated in vacuo. The residue was purified via flash chromatography on silica gel(80:20, Hexane/EtOAc) to afford tosylhydrazone 7 as white solid in 92% yield (0.13 g, 0.22 mmol); mp 162-165° C. $^1$H-NMR (400 MHz, $CDCl_3$) δ 8.02-7.79 (m, 3H), 7.46 (d, J=9.5 Hz, 2H), 7.36 (t, J=8.7 Hz, 3H), 7.14 (t, J=7.7 Hz, 1H), 5.28 (s, 1H), 5.07 (d, J=9.8 Hz, 1H), 4.70 (s, 1H), 4.48 (s, 1H), 4.25 (q, J=7.1 Hz, 2H), 2.99 (s, 1H), 2.58-2.34 (m, 6H), 2.10-1.85 (m, 4H), 1.34 (t, J=7.1 Hz, 3H), 1.22 (s, 3H). $^{13}$C-NMR (101 MHz, $CDCl_3$) δ 170.44, 153.31, 144.28, 143.92, 142.66, 138.39, 135.01, 132.51, 129.73, 129.69, 129.49, 128.25, 127.80, 127.78, 124.74, 114.17, 85.49, 78.23, 77.35, 77.04, 76.72, 61.70, 49.10, 44.80, 29.37, 21.66, 18.00, 14.18, 13.07. IR (film) 3210, 3070, 2980, 2919, 2256, 1739, 1442, 1402 cm*HRMS Calcd for $C_{28}H_{31}BrN_2NaO_5S^+$: 587.1215. Found: 587.1201.

Example 28

Ester 8. Catecholborane (0.10 mL, 0.80 mmol)) was added to a solution of tosylhydrazone 7 (0.40 g, 0.70 mmol) in $CHCl_3$ (3.00 mL) at 0° C. The reaction mixture was stirred at 0° C. for 1 h, then NaOAc.3$H_2O$ (0.19 g, 1.30 mmol) was added in one portion. The reaction mixture was maintained for 1 h at 0° C., diluted with $CHCl_3$ (1.80 mL), and heated under reflux for 12 h. The mixture was then cooled to rt and filtered through a pad of Celite. The filtrate was concentrated in vacuo and the residue was purified via flash chromatography over silica gel (90:10, hexanes/EtOAc) to afford reduced ester 8 as white solid in 68% yield (0.17 g, 0.48 mmol); mp 37-40° C.; $^1$H-NMR (270 MHz, $CDCl_3$) δ 7.97 (d, J=6.2 Hz, 1H), 7.49 (d, J=8.0 Hz, 1H), 7.36 (t, J=7.0 Hz, 1H), 7.12 (t, J=7.6 Hz, 1H), 5.59 (s, 1H), 5.34 (d, J=6.4 Hz, 1H), 4.79 (s, 2H), 4.38 (d, J=6.4 Hz, 1H), 4.25 (dd, J=4.9, 7.1 Hz, 2H), 3.01 (s, 1H), 2.37 (m, 3H), 2.21-2.04 (m, 1H), 1.73 (s, 3H), 1.60 (s, 4H), 1.31 (t, J=7.1 Hz, 3H). $^{13}$C-NMR (67 MHz, $CDCl_3$) δ 173.01, 146.94, 140.85, 132.70, 130.21, 129.58, 129.37, 128.04, 123.25, 123.10, 112.16, 83:50, 81.30, 77.56, 77.09, 76.62, 61.33, 49.14, 47.31, 39.39, 28.04, 22.08, 21.00, 14.22.

Example 29

Methyl ester 5a.i. Into a 25 mL round bottom flask was placed 100 mg (0.24 mmol) ethyl ester 5a, 15 mL methanol (11.85 g, 370 mmol) and a magnetic stir bar. To the mixture was added 0.04 g (0.28 mmol, 1.2 eq) $K_2CO_3$ and the reaction was allowed to stir at room temperature. After ~20 min the mixture turned from a very light yellow color to dark orange and TLC revealed no starting material remained. The mixture was then transferred to a seperatory funnel and diluted with 10 mL $H_2O$ and extracted with $CH_2Cl_2$ (3×20 mL). The combined organic extracts were washed with brine (50 mL), extracted with $CH_2Cl_2$ (40 mL), dried over $MgSO_4$, and concentrated in vacuo. The crude product was filtered through a short silica gel column eluted with EtOAc/Hexanes (50:50) to deliver methyl ester 5a.i as a colorless oil (94.8 mg, 23.3 mg, 97%). $^1$H-NMR (270 MHz, $CDCl_3$) δ8.32-8.28 (d, 1H), 7.55-7.52 (d, 1H), 7.48-7.42 (t, 1H), 7.22-7.16 (t, 1H), 5.82-5.78 (m, 1H), 5.27-5.23 (d, 1H), 4.87-4.84 (m, 2H), 4.51 (s, 1H), 3.85 (s, 3H), 2.93 (s, 1H), 2.80-2.73 (m, 1H), 2.65-2.53 (m, 1H), 2.38-2.26 (m, 2H), 1.88 (s, 1H), 1.59 (s, 1H).

Example 30

Cyclopropylmethyl ester 5a.ii. Into an 8 mL microwave vessel was placed 0.14 g (0.33 mmol) ethyl ester 5a and a magnetic stir bar. Added to the starting material was 2.66 mL (100 eq, 33.22 mmol) cyclopropyl methanol followed by 0.063 g (0.75 eq, 0.241) Bu$_2$SnO. The vessel was sealed and reacted in a microwave reactor for 30 min. at 150° C. and 300 watts of power with continuous stirring. The reaction was diluted with 10 mL ethyl acetate and transferred to a separatory funnel, washed with saturated NaHCO$_3$ (30 mL) and extracted with EtOAc (3×20 mL). The combined organic extracts were then washed with brine, dried over MgSO$_4$, and concentrated in vacuo. The crude product was purified on a silica gel column eluted with EtOAc/Hexanes (10:90) to deliver ester 5a.ii as a colorless oil (0.125 g, 0.28 mmol, 84%). $^1$H-NMR (270 MHz, CDCl$_3$) δ8.31-8.26 (d, 1H), 7.55-7.50 (d, 1H), 7.46-7.39 (m, 1H), 7.21-7.14 (m, 1H), 5.81-5.75 (m, 1H), 5.28-5.23 (d, 1H), 4.84 (s, 2H), 4.48 (s, 1H), 4.15-4.01 (m, 2H), 3.16 (s, 1H), 2.80-2.74 (m, 1H), 2.59-2.45 (m, 1H), 2.36-2.24 (m, 2H), 1.87 (s, 3H), 1.57 (s, 3H), 1.29-1.14 (m, 1H), 0.65-0.57 (m, 2H), 0.38-0.31 (m, 2H). $^{13}$C-NMR (270 MHz, CDCl$_3$) 171.0, 146.8, 139.4, 132.9, 132.4, 130.4, 129.7, 128.3, 125.7, 112.2, 82.7, 81.9, 80.7, 70.2, 55.5, 39.5, 27.8, 21.27, 17.7, 9.6, 3.4.

Example 31

Cyclopentylmethyl ester 5a.iii. Ester 5a.iii was prepared as above for 5a.ii in 91% yield (0.11 g, 0.24 mmol) from 0.11 g (0.26 mmol) of ester 5a. $^1$H-NMR (270 MHz, CDCl$_3$) 8.29 (d, J=6.2 Hz, 1H), 7.53 (d, J=8.0 Hz, 1H), 7.44 (t, J=7.5 Hz, 1H), 7.19 (dd, J=4.5, 10.8 Hz, 1H) 5.79 (s, 1H), 5.25 (d, J=9.0 Hz, 1H), 4.85 (s, 2H), 4.49 (s, 1H), 4.17-4.04 (m, 2H), 2.99 (s, 1H), 2.76 (dd, J=5.0, 9.1 Hz, 1H), 2.64-2.52 (m, 1H), 2.32 (d, J=7.3 Hz, 3H); 1.89-1.74 (m, 6H), 1.68-1.54 (m, 8H), 1.39-1.26 (m, 3H). $^{13}$C-NMR (67 MHz, CDCl$_3$) 171.1, 147.1, 139.5, 132.9, 132.4, 130.3, 129.7, 128.3, 125.5, 123.8, 112.0, 82.5, 81.9, 80.6, 69.3, 55.5, 38.5, 38.3, 29.3, 27.5, 25.4, 21.5, 17.6.

Example 32

Acid 9. To a solution of 3:2:1 THF/H$_2$O/MeOH and 0.180 g (0.43 mmol) ester 5a was added 0.02 g (0.85 mmol, 2 eq) LiOH at rt. The reaction mixture was allowed to stir at rt ~1.5 h until no starting material was observed by TLC. The solution was then titrated to pH~2 with 3N HCl and diluted with CH$_2$Cl$_2$ (30 mL). The mixture was transferred to a separatory funnel, extracted with CH$_2$Cl$_2$ (3×30 mL), and the combined extracts washed with brine (40 mL). The combined organic extracts were dried over MgSO$_4$ and concentrated in vacuo to yield a yellow foam which was filtered through a plug of silica gel (50:50 EtOAc/Hexane) to produce acid 9 as a white powder (159 mg, 0.406 mmol 95%). $^1$H-NMR (270 MHz, CDCl$_3$) δ 8.14-8.09 (d, 1H), 7.59-7.54 (d, 1H), 7.47-7.40 (t, 1H), 7.25-7.18 (t, 1H), 5.81 (s, 1H), 5.28 (s, 1H), 5.25 (d, 1H), 4.85 (s, 2H), 4.51 (s, 1H), 2.79-2.72 (dd, 1H), 2.60-2.47 (m, 1H), 2.35-2.24 (m, 2H), 1.94 (s, 3H), 1.59 (s, 3H). $^{13}$C-NMR (270 MHz, CDCl$_3$) 146.6, 138.6, 132.9, 132.7, 130.0, 129, 128.4, 125.9, 124.1, 112.4, 82.7, 55.6, 27.6, 21.4, 17.7.

Example 33

Diene 10a. Preparation was carried out as above for 5a from glycolate 4a (3.5 g, 8.31 mmol), but the reaction mixture was allowed to stir for 5 minutes before quenching with HOAc. Purification of the crude product via flash chromatography over silica gel (10:90 EtOAc/hexanes) delivered diene 10a as a yellow oil in 15% yield (0.42 g, 1.27 mmol) as well as isobenzofuran 5a in 41% yield (1.43 g, 3.41 mmol).

$^1$H-NMR (400 MHz, CDCl$_3$) δ 7.64 (d, J=6.5, 1H), 7.34-7.08 (m, 3H), 6.62 (s, 1H), 4.95 (s, 1H), 4.73 (s, 1H), 3.62 (s, 1H), 2.74-2.48 (m, 1H), 2.19 (s, 1H), 1.95-1.82 (m, 2H), 1.77 (s, 2H), 1.59 (s, 1H). $^{13}$C-NMR (101 MHz, CDCl$_3$) δ 189.40, 145.37, 141.23, 139.35, 136.66, 136.31, 134.83, 132.82, 129.65, 129.62, 127.04, 125.00, 114.21, 77.35, 77.03, 76.71, 43.88, 29.72, 29.18, 21.78, 16.34.

Example 34

Diene 10e. Diene 10e was prepared as above for 10a and was obtained in 33% yield (0.10 g, 0.33 mmol) from 0.41 g (1.08 mmol) of glycolate 4e. $^1$H-NMR (300 MHz, CDCl$_3$) δ 8.34 (d, J=8.0 Hz, 1H), 8.16 (d, J=7.2 Hz, 1H), 7.86 (dd, J=8.2, 10.1 Hz, 2H), 7.61-7.42 (m, 3H), 5.76 (s, 1H), 5.62 (d, J=7.2 Hz, 1H), 4.87 (d, J=26.1 Hz, 2H), 4.59 (s, 1H), 3.83 (s, 3H), 3.26 (s, 1H), 3.03 (t, J=7.2 Hz, 1H), 2.39 (dd, J=6.5, 12.7 Hz, 1H), 2.34-2.21 (m, 2H), 1.87 (s, 3H), 1.55 (s, 3H). $^{13}$C-NMR (75 MHz, CDCl$_3$) δ 189.94, 146.02, 141.49, 140.18, 136.87, 133.88, 133.65, 133.24, 132.32, 128.97, 128.70, 126.58, 126.32, 126.02, 125.37, 124.92, 114.15, 44.28, 29.57, 22.06, 16.59. Calcd for C$_{22}$H$_{22}$O: C, 87.38; H, 7.33. Found: C, 87.78; H, 7.26.

Example 35

Diene 10g. Diene 10g was prepared as above for 10a and was obtained in 41% yield (0.05 g, 0.19 mmol) from 0.15 g (0.46 mmol) of glycolate 4g. $^1$H-NMR (300 MHz, CDCl$_3$) δ 7.50 (d, J=1.6 Hz, 1H), 7.42 (s, 1H), 6.70-6.61 (m, 1H), 6.58 (d, J=3.4 Hz, 1H), 6.47 (dd, J=1.8, 3.4 Hz, 1H), 4.87-4.74 (m, 1H), 4.65 (s, 1H), 4.37 (d, J=6.1 Hz, 1H), 2.77-2.45 (m, 2H), 1.86 (s, 3H), 1.81 (s, 3H). $^{13}$C-NMR (75 MHz, CDCl$_3$) δ 188.77, 152.31, 145.57, 144.27, 141.82, 136.68, 134.43, 122.87, 116.05, 112.65, 112.24, 43.29, 28.94, 22.11, 16.77. Calcd for C$_{16}$H$_{18}$O$_2$: C, 79.31; H, 7.49. Found: C, 79.23; H, 7.24.

Example 36

Diene 10h. Diene 10h was prepared as above for 10a and was obtained in 45% yield (0.07 g, 0.26 mmol) from 0.20 g (0.58 mmol) of glycolate 4h. $^1$H NMR (300 MHz, CDCl$_3$) δ 7.68 (s, 1H), 7.33 (dt, J=4.5, 14.2 Hz, 2H), 7.12 (dd, J=8.3, 16.2 Hz, 2H), 6.67-6.59 (m, 1H), 4.96 (s, 1H), 4.74 (s, 1H), 3.75 (s, 1H), 2.72-2.50 (m, 2H), 1.90 (s, 3H), 1.81 (s, 3H). $^{13}$C-NMR (75 MHz, CDCl$_3$) δ 189.45, 162.81, 159.50, 145.36, 141.33, 140.24, 136.68, 130.42, 130.31, 129.93, 129.90, 128.54, 128.49, 124.03, 123.98, 123.86, 115.88, 115.59, 114.30, 44.28, 29.24, 21.92, 16.50. Calcd for C$_{18}$H$_{19}$FO: C, 79.97; H, 7.08. Found: C, 79.58; H, 6.72.

Example 37

Isobenzofuran 51. A solution of isobenzofuran 5f (0.13 g, 0.394 mmol) and iodomethane (ca. 20 eq) was heated under reflux in MeCN. After 3 days, the reaction mixture was cooled and concentrated under the reduced pressure to give pyridinium iodide 51 in 98% yield (0.18 g, 0.39 mmol). $^1$H-NMR (300 MHz, CDCl$_3$) δ 9.48 (d, J=8.4 Hz, 1H), 8.82 (d, J=6.2 Hz, 1H), 8.33 (t, J=8.0 Hz, 1H), 7.85 (t, J=6.2 Hz, 1H), 5.61 (s, 1H), 5.48 (s, 1H), 5.05 (d, J=7.6 Hz, 2H), 4.71 (d, J=1.8 Hz, 1H), 4.38 (s, 3H), 3.94 (d, J=12.1 Hz, 1H), 3.85-3.69 (m, 4H), 2.63 (dd, J=5.6, 11.8 Hz, 1H), 2.46 (d, J=17.9 Hz, 1H), 1.80 (d, J=16.3 Hz, 6H). $^{13}$C-NMR (75 MHz, CDCl$_3$) δ 170.15, 159.52, 145.70, 144.41, 133.23, 130.75, 126.42, 125.31, 116.53, 86.99, 83.31, 80.34, 52.75, 52.38, 46.23, 45.65, 29.89, 19.97, 18.17. Calcd for $C_{20}H_{26}INO_4$: C, 50.97; H, 5.56. Found: C, 51.11; H, 5.65.

Example 38

Cell Proliferation Studies

Inhibition of cell proliferation was assessed by the MTT assay. This assay is based on the ability of a mitochondrial dehydrogenase enzyme from viable cells to cleave the tetrazolium rings of the pale yellow 3-(4,5-dimethylthiazol-2-yl)-2,5-diphenyltetrazolium bromide (MTT) and form a dark blue formazan crystal product which is largely impermeable to cell membranes, thus resulting in its accumulation within healthy cells.(22) Solubilization of the cells by the addition of solvent results in the liberation of the crystals which are solubilized. The level of the formazan product created is directly proportional to the number of living cells.(23,24)

All stock solutions of compounds were made at 10 mM in dimethyl sulfoxide (DMSO). DMSO and MTT were from Sigma Chemical Co. (St. Louis, Mo.). Cell culture reagents were obtained from Life Technologies (Carlsbad, Calif.). The KB-3 human carcinoma cell line was maintained in monolayer culture at 37° C. and 5% $CO_2$ in Dulbecco's Modified Eagle's Medium, supplemented with 10% fetal bovine serum, 2 mM L-glutamine, 50 units/mL penicillin, and 50 μg/mL streptomycin.

KB-3 cells (2000/well) were plated in 96-well dishes, and after 24 h were treated with 0.1 nM-100 μM of the compound in question. The final concentration of DMSO did not exceed 1%, and controls received vehicle alone. After 96 h, cells were incubated with 50 μg MTT/well/0.2 mL for 4 h at 37° C., the media was removed, and the formazan crystals were dissolved in 0.15 mL of DMSO. Absorbance at 570 nm was measured with an ELx800™ Microplate Reader (Bio Tek Instruments, Inc., Winooski, Vt.). All treatments were performed in triplicate. Results are shown in FIGS. 1A-D as a percentage of control samples (mean±SD). $IC_{50}$ is the concentration that reduced survival to 50% of the control (no drug).

The present invention has been described hereinabove with reference to particular examples for purposes of clarity and understanding rather than by way of limitation. It should be appreciated that certain improvements and modifications can be practiced within the scope of the appended claims.

REFERENCES

The pertinent portions of the following references are incorporated herein by reference.

1. *Cyclized Cembranoids of Natural Occurrence* Wahlberg, I.; Eklund, A.-M. *Prog. Chem. Org. Nat. Prod.* 1992, 60, 1-141; *Survey of Oxygenated 2,11-Cyclized Cembranoids of Marine Origin* Bernardelli, P.; Paquette, L. A. *Heterocycles* 1998, 49, 531-556.
2. *Sclerophytins A and B. Isolation and Structures of Novel Cytotoxic Diterpenes from the Marine Coral Sclerophytum capitalis* Sharma, P.; Alam, M. *J. Chem. Soc. Perkin Trans* 11988, 2537-2540.
3. Structure revision: *Revised Constitution of Sclerophytins A and B* Friedrich, D.; Doskotch, R. W.; Paquette, L. A. *Org. Lett.* 2000, 2, 1879-1882; *Structural and stereochemical reassessment of sclerophytin-type diterpenes* Friedrich, D.; Paquette, L. A. *J. Nat. Prod.* 2002, 65, 126-130.
4. Total syntheses: *Total Asymmetric Synthesis of the Putative Structure of the Cytotoxic Diterpenoid (−)-Sclerophytin A and of the Authentic Natural Sclerophytins A and B* Bernardelli, P.; Moradei, O. M.; Friedrich, D.; Yang, J.; Gallou, F.; Dyck, B. P.; Doskotch, R. W.; Lange, T.; Paquette, L. A. *J. Am. Chem. Soc.* 2001, 123, 9021-9032; *A General Strategy for the Synthesis of Cladiellin Diterpenes Enantioselective Total Syntheses of 6-Acetoxycladiell-7(16), 1'-dien-3-ol (Deacetoxyalcyonin Acetate), Cladiell-1'-ene-3,6,7-triol, Sclerophytin A, and the Initially Purported Structure of Sclerophytin A* MacMillan, D. W. C.; Overman, L. E.; Pennington, L. D. *Journal of the American Chemical Society* 2001, 123, 9033-9044. See also, *A General Strategy for Synthesis of Both (6Z)-and (6E)-Cladiellin Diterpenes: Total Syntheses of (−)-Cladiella-6,11-dien-3-ol, (+)-Polyanthellin A, (−)-Cladiell-11-ene-3,6,7-triol, and (−)Deacetoxyalcyonin Acetate*. Kim, H.; Lee, H.; Kim, J.; Kim, S.; Kim, D. *J. Am. Chem. Soc.* 2006, 128, 15851-15855.
5. *Eleutherobin, a New Cytotoxin that Mimics Paclitaxel (Taxol) by Stabilizing Microtubules* Lindel, T.; Jensen, P. R.; Fenical, W.; Long, B. H.; Casazza, A. M.; Carboni, J.; Fairchild, C. R. *J. Am. Chem. Soc.* 1997, 119, 8744-8745.
6. Total syntheses: *Total Synthesis of Eleutherobin and Eleuthosides A and B* Nicolaou, K. C.; Ohshima, T.; Hosokawa, S.; van Delft, F. L.; Vourloumis, D.; Xu, J. Y.; Pfefferkorn, J.; Kim, S. *J. Am. Chem. Soc.* 1998, 120, 8674-8680; *The Total Synthesis of Eleutherobin* Chen, X.-T.; Bhattacharya, S. K.; Zhou, B.; Gutteridge, C. E.; Pettus, T. R. R.; Danishefsky, S. J. *J. Am. Chem. Soc.* 1999, 121, 6563-6579.
7. *Sarcodictyin A and sarcodictyin B, novel diterpenoidic alcohols esterified by (E)-N(1)-methylurocanic acid. Isolation from the Mediterranean stolonifer Sarcodictyon roseum* D'Ambrosio, M.; Guerriero, A.; Pietra, F. *Helv. Chim. Acta* 1987, 70, 2019-2027; *Isolation from the Mediterranean stoloniferan coral Sarcodictyon roseum of sarcodictyin C, D, E, and F, novel diterpenoidic alcohols esterified by (E)-or(Z)-N(1)-methylurocanic acid. Failure of the carbon-skeleton type as a classification criterion* D'Ambrosio, M.; Guerriero, A.; Pietra, F. *Helv. Chim. Acta* 1988, 71, 964-976.
8. Total synthesis: *Total Synthesis of Sarcodictyins A and B* Nicolaou, K. C.; Xu, J. Y.; Kim, S.; Pfefferkorn, J.; Ohshima, T.; Vourloumis, D.; Hosokawa, S. *J. Am. Chem. Soc.* 1998, 120, 8661-8673;
9. *Cell-based screen for antimitotic agents and identification of analogues of rhizoxin, eleutherobin, and paclitaxel in natural extracts* Roberge, M.; Cinel, B.; Anderson, H. J.; Lim, L.; Jiang, X.; Xu, L.; Bigg, C. M.; Kelly, M. T.; Andersen, R. J. *Cancer Res.* 2000, 60, 5052-5058.
10. *Sarcodictyins: a New Class of Marine Derivatives with Mode of Action Similar to Taxol* Ciomei, M.; Albanese, C.; Pastori, W.; Grandi, M.; Pietra, F.; D'Ambrosio, M.; Guerriero, A.; Battistini, C. *Proc. Am. Assoc. Cancer Res.* 1998, 38, 30; *The Coral-derived Natural Products Eleutherobin and Sarcodictyins A and B: Effects on the Assembly of Purified Tubulin with and without Microtubule-associated Proteins and Binding at the Polymer Taxoid Site.* Hamel, E.; Sackett, D. L.; Vourloumis, D.; Nicolaou, K. C. *Biochemistry* 1999, 38, 5490-5498.
11. *Solid and Solution Phase Synthesis and Biological Evaluation of Combinatorial Sarcodictyin Libraries* Nicolaou, K. C.; Winssinger, N.; Vourloumis, D.; Ohshima, T.; Kim, S.; Pfefferkorn, J.; Xu, J. Y.; Li, T. *J. Am. Chem. Soc.* 1998, 120, 10814-10826.
12. *Synthesis of novel simplified sarcodictyin/eleutherobin analogs with potent microtubule-stabilizing activity, using ring closing metathesis as the key-step* Beumer, R.; Bayon, P.; Bugada, P.; Ducki, S.; Mongelli, N.; Sirtori, F. R.; Telser, J.; Gennari, C. *Tetrahedron* 2003, 59, 8803-8820.

13. *Structure-activity Profiles of Eleutherobin Analogs and their Cross-resistance in Taxol-resistant Cell Lines* McDaid, H. M.; Bhattacharya, S. K.; Chen, X. T.; He, L.; Shen, H. J.; Gutteridge, C. E.; Horwitz, S. B.; Danishefsky, S. J. *Cancer Chemother. Pharmacol.* 1999, 44, 131-137.

14. *Synthetic Transformations of Eleutherobin Reveal New Features of Its Microtubule-Stabilizing Pharmacophore* Britton, R.; Dilip de Silva, E.; Bigg, C. M.; McHardy, L. M.; Roberge, M.; Andersen, R. J. *J. Am. Chem. Soc.* 2001, 123, 8632-8633.

15. *Synthesis of a simplified analogue of eleutherobin via a Claisen rearrangement and ring closing metathesis strategy* Chiang, G. C. H.; Bond, A. D.; Ayscough, A.; Pain, G.; Ducki, S.; Holmes, A. B. *Chem. Commun.* 2005, 1860-1862.

16. *Design, synthesis and cytotoxic studies on the simplified oxy analog of eleutherobin* Chandrasekhar, S.; Jagadeshwar, V.; Narsihmulu, C.; Sarangapani, M.; Krishna, D. R.; Vidyasagar, J.; Vijay, D.; Sastry, G. N. *Bioorg. Med. Chem. Lett.* 2004, 14, 3687-3689.

17. See also, *Synthetic Approach to Analogues of the Original Structure of Sclerophytin A* Jung, M. E.; Pontillo, J. *J. Org. Chem.* 2002, 67, 6848-6851.

18. Davidson, J. E. P.; Gilmour, R.; Ducki, S.; Davies, J. E.; Green, R.; Burton, J. W.; Holmes, A. B. *Synlett* 2004, 1434-1435; see also, Chiang, G. C. H.; Bond, A. D.; Ayscough, A.; Pain, G.; Ducki, S.; Holmes, A. B. *Chem. Commun.* 2005, 1860-1862.

19. (a) *A Novel Cycloaldol Approach to the Isobenzofuran Core of the Eunicellin Diterpenes* Chai, Y.; Vicic, D. A.; McIntosh, M. C. *Org. Lett.* 2003, 7, 1039-1042. (b) *Studies directed toward the synthesis of the massileunicellins* Chai, Y.; McIntosh, M. C. *Tetrahedron Lett.* 2004, 45, 3269-3272. (c) Hutchison, J. M.; Lindsay, H. A.; Dormi, S. S.; Jones, G. D.; Vicic, D. A.; McIntosh, M. C. *Org. Lett.* 2006, 8, 3663-3665.

20. *Direct Oxidation of Tertiary Allylic Alcohols. A Simple and Effective Method for Alkylative Carbonyl Transposition* Dauben, W. G.; Michno, D. M. *J. Org. Chem.* 1977, 42, 682-685.

21. *Benzyl Enol Ethers via Decarboxylation of a-Benzyloxy-b-lactones Derived from the Lithium a-Benzyloxy-a-lithioacetate Synthon* Adam, W.; Arias Encarnacion, L. A. *Synthesis* 1979, 388-390.

22. *Rapid colorimetric assay for cellular growth and survival: application to proliferation and cytotoxicity assays.* Mosmann T. *J. Immunol. Methods* 1983, 65, 55-63.

23. *Modulation of mitogen-activated protein kinases and phosphorylation of Bcl-2 by vinblastine represent persistent forms of normal fluctuations at G2-M1.* Fan, M.; Du, L.; Stone, A. A.; Gilbert K. M.; Chambers, T. C. *Cancer Res.* 2000, 60, 6403-6407.

24. *Feasibility of drug screening with panels of human tumor cell lines using a microculture tetrazolium assay.* Alley, M. C.; Scudiero, D. A.; Monks A.; Hursey, M. L.; Czerwinski, M. J.; Fine, D. L.; Abbott, B. J.; Mayo, J. G.; Shoemaker, R. H.; Boyd M. R. *Cancer Res.* 1988, 48, 589-601.

What is claimed is:

1. A compound having a structural formula selected from the following:

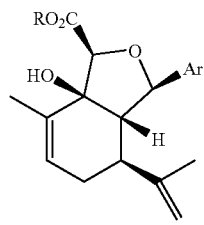

5

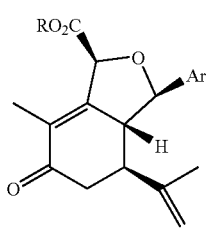

6

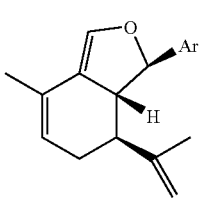

10 wherein R represents 14, substituted lower alkyl, or unsubstituted lower alkyl; Ar represents a substituted or unsubstituted aryl; and pharmaceutically acceptable esters and salts thereof.

2. A compound of claim 1, wherein R=methyl, ethyl, cyclopropylmethyl or cyclopentylmethyl.

3. A compound of claim 1, wherein Ar=2-Br-phenyl, 3-Br-phenyl, 2,3-di-Cl-phenyl, 2,4-di-Cl-phenyl, 1-naphthyl, 2-pyridyl, 2-furyl, or 2-fluorophenyl.

4. A compound of claim 1 having structure 10, wherein Ar=2-fluorophenyl.

5. A method of converting (S)-(+)-carvone to an aryl glycolate compound thereof, comprising:
   (i) reacting (S)-(+)-carvone with an arylaldehyde in an aldol condensation reaction to afford an aryl anti-alcohol; and
   (ii) etherifying the aryl anti-alcohol to afford said aryl glycolate compound.

6. The method of claim 5, further comprising cyclizing said aryl glycolate to afford an isobenzofuran having the structural formula

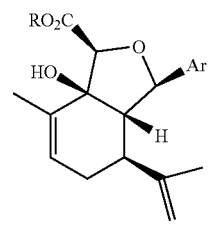

wherein R represents H, substituted lower alkyl, or unsubstituted lower alkyl; and Ar represents a substituted or unsubstituted aryl.

7. The method of claim 6, further comprising converting by oxidative rearrangement said isobenzofuran to an enone having the structural formula

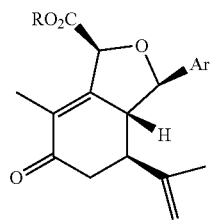

wherein R represents H, substituted lower alkyl, or unsubstituted lower alkyl; and Ar represents a substituted or unsubstituted aryl.

8. The method of claim 5, further comprising converting by β-lactonization-decarboxylation said aryl glycolate to a diene having the structural formula

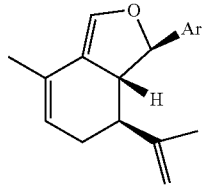

wherein Ar represents a substituted or unsubstituted aryl.

9. A method of inhibiting cell growth comprising contacting cancerous cells with a growth inhibiting amount of a compound of claim 1, wherein the cancerous cells comprise leukemia, prostate, or non-small cell lung cancer cells.

10. A method of inhibiting cell proliferation in a patient comprising administering to the patient a proliferation-inhibiting amount of a compound of claim 1, wherein the patient suffers from cancer comprising leukemia, prostate, or non-small cell lung cancer.

* * * * *